United States Patent
Nan et al.

(10) Patent No.: US 10,196,389 B2
(45) Date of Patent: Feb. 5, 2019

(54) ONE CLASS OF PYRAZOLONE COMPOUNDS AND USE THEREOF

(71) Applicant: SHANGHAI INSTITUTE OF MATERIA MEDICA, CHINESE ACADEMY OF SCIENCES, Shanghai (CN)

(72) Inventors: Fajun Nan, Shanghai (CN); Jia Li, Shanghai (CN); Jingya Li, Shanghai (CN); Mei Zhang, Shanghai (CN); Dakai Chen, Shanghai (CN); Lina Zhang, Shanghai (CN); Runtao Zhang, Shanghai (CN); Zhifu Xie, Shanghai (CN)

(73) Assignee: SHANGHAI INSTITUTE OF MATERIA MEDICA, CHINESE ACADEMY OF SCIENCES, Zhangjiang, Pudong, Shanghai (CN)

( * ) Notice: Subject to any disclaimer, the term of this patent is extended or adjusted under 35 U.S.C. 154(b) by 0 days.

(21) Appl. No.: 15/326,310

(22) PCT Filed: Jul. 14, 2015

(86) PCT No.: PCT/CN2015/084006
§ 371 (c)(1),
(2) Date: May 1, 2017

(87) PCT Pub. No.: WO2016/008404
PCT Pub. Date: Jan. 21, 2016

(65) Prior Publication Data
US 2017/0247371 A1    Aug. 31, 2017

(30) Foreign Application Priority Data

Jul. 14, 2014    (CN) .......................... 2014 1 0334467

(51) Int. Cl.
| | |
|---|---|
| A61K 31/437 | (2006.01) |
| C07D 401/14 | (2006.01) |
| C07D 471/04 | (2006.01) |
| C07D 211/78 | (2006.01) |
| C12N 9/12 | (2006.01) |

(52) U.S. Cl.
CPC .......... *C07D 471/04* (2013.01); *A61K 31/437* (2013.01); *C07D 211/78* (2013.01); *C12N 9/12* (2013.01); *C12Y 207/11031* (2013.01)

(58) Field of Classification Search
CPC ........................... C07D 401/14; A61K 31/437
USPC .......................................... 546/119; 514/303
See application file for complete search history.

(56) References Cited

U.S. PATENT DOCUMENTS 8,865,758 B2 * 10/2014 Page .................... C07D 471/04
424/400

FOREIGN PATENT DOCUMENTS

| CN | 102762563 A | 10/2012 |
|---|---|---|
| WO | 2011049731 A1 | 4/2011 |

OTHER PUBLICATIONS

Int'l Search Report dated Oct. 19, 2015 in Int'l Application No. PCT/CN2015/084006.

* cited by examiner

*Primary Examiner* — Niloofar Rahmani
(74) *Attorney, Agent, or Firm* — Panitch Schwarze Belisario & Nadel LLP

(57) ABSTRACT

Provided are a class of pyrazolone compounds and a use thereof. In particular, a compound represented by formula I is provided, wherein the definition of each variable group is as described in the description. The compounds of formula (I) have a direct AMPK-activating activity and can significantly promote the phosphorylation of AMPK and ACC of L6 myocytes and HepG2 cells in a dose-dependent manner.

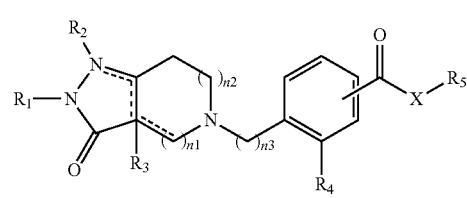

15 Claims, 3 Drawing Sheets

ONE CLASS OF PYRAZOLONE COMPOUNDS AND USE THEREOF

CROSS-REFERENCE TO RELATED APPLICATION

This application is a Section 371 of International Application No. PCT/CN2015/084006, filed Jul. 14, 2015, which was published in the Chinese language on Jan. 21, 2016, under International Publication No. WO 2016/008404 A1, and the disclosure of which is incorporated herein by reference.

FIELD OF THE INVENTION

The present invention belongs to field of pharmaceutical chemistry, and relates to a class of pyrazolone compounds, the preparation methods thereof, and the pharmaceutical compositions containing the compound.

BACKGROUND OF THE INVENTION

Diabetes is a series of metabolic disorders syndrome induced by factors such as body islet dysfunction and insulin resistance. Multiple pathogenic factors such as genetic factors, immune dysfunction, and mental factors can cause diabetes. According to the World Health Organization statistics, by 2011, there are about 346 million people suffering from diabetes. In 2004, about 3.4 million people died of high blood sugar, and more than 80% of diabetes deaths occur in low- and middle-income countries.

There are now many drugs for the treatment of type II diabetes, including metformin, sulfonylureas, DPP-4 inhibitors, PPARγ agonists, α-glucosidase inhibitors, insulin and GLP-1 analogues. However, the existing medicines have certain problems such as no significant effect, short duration time. Some drugs even have side effects such as hypoglycemia, weight gain, edema, fractures, lactic acidosis and gastrointestinal discomfort.

Adenosine monophosphate activated protein kinase (AMPK) plays an important role in metabolism of glucose and lipid in vivo. It is an energy meter and metabolic main switch reflecting the change of intracellular energy state. Its activation can significantly improve metabolism of glucose and lipid in type 2 diabetes, enhance activity of insulin sensitivity, and has been confirmed as a new target for treatment of type 2 diabetes. Studies have shown that many known drugs or natural products for treatment of type 2 diabetes have been found to indirectly activate AMPK in vivo, and the therapeutic effect may be partially due to activation of AMPK, but these indirect activators have side effects such as gastrointestinal discomfort and weight gain. Therefore, it will be an effective way to find treatment for type II diabetes by finding and discovering small molecule activators of AMPK, especially small molecule activators directly acting on AMPK.

Therefore, there is an urgent need to provide novel AMPK activators with less side effects.

SUMMARY OF THE INVENTION

The object of the present invention is to provide novel AMPK activators with less side effects.

In the first aspect of the present invention, a compound of formula I, or a pharmaceutically acceptable salt thereof is provided,

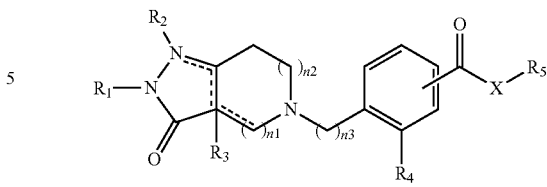

wherein $R_1$ is selected from the group consisting of: H, C1-C4 alkyl, 6- to 12-membered aryl group or 5-10 membered heteroaryl in which the hydrogen atoms on the group are optionally substituted with one or more substituents selected from the group consisting of: halogen, C1-C4 alkyl, C1 to C4 halogen substituted alkyl, adamantyl, hydroxyl, amino, nitro, substituted or unsubstituted acetoxy group (AcO), carboxyl, C1-C4 alkoxy, C1-C4 haloalkoxy, cyano, substituted or unsubstituted phenyl, —$SO_2$—$NH_2$; wherein the term "substituted" refers to that one or more hydrogen atoms on a group are substituted with a substituent selected from the group consisting of: halogen, trifluoromethyl, hydroxy, amino, C1-4 alkyl, C1-C4 alkoxy, adamantyl, and cyano;

$R_2$ is selected from the group consisting of H, and C1-C4 alkyl, or $R_2$ is none;

$R_3$ is selected from the group consisting of H, and C1-C4 alkyl, or $R_3$ is none;

$R_4$ is selected from the group consisting of: H, C1-C4 alkyl, C1-C4 haloalkyl, halogen, hydroxy, amino, nitro, AcO, carboxyl, C1-C4 alkoxy, and cyano;

$R_5$ is selected from the group consisting of: H, C1-C4 alkyl, C3-C7 cycloalkyl, C1-C4 alkylene-C3-C7 cycloalkyl, phenyl, C1-C4 alkylene phenyl, wherein the hydrogen on phenyl or C1-C4 alkylene phenyl can be optionally substituted by one or more substituents selected from the group consisting of: hydroxy, halogen, C1-C4 alkyl, C1-C4 haloalkyl, C3-C7 cycloalkyl, C1-C4 alkoxy, C1-C4 haloalkoxy; wherein when R5 is a phenyl-containing group, the hydrogen atoms of two adjacent carbons on the phenyl are optionally substituted by "—O—$(CH_2)_n$O—", wherein n=1, 2 or 3;

n1 is 0, 1, or 2;
n2 is 0, 1, 2, or 3;
n3 is 0, 1, or 2;

X is selected from the group consisting of: O, and $NR_B$, wherein $R_8$ is selected from the group consisting of: H, C1-C4 alkyl, C1-C4 haloalkyl, C3-C7 cycloalkyl, phenyl, and C1-C4 alkylene phenyl; and a dashed line is a chemical bond or none.

In another preferred embodiment, C1-C4 haloalkyl comprises C1-C4 fluoro group, and preferably trifluoromethyl group.

In another preferred embodiment, $R_1$ is a phenyl substituted with 1 to 5 substituents selected from the group consisting of halogen and trifluoromethyl.

In another preferred embodiment, the 6-12 membered aryl is phenyl or naphthyl.

In another preferred embodiment, the C1-C4 alkylene phenyl includes benzyl, —C (cyclopropyl)-phenyl.

In another preferred embodiment, $R_1$ is selected from the group consisting of: 6- to 12-membered aryl group or 5-10 membered heteroaryl group in which the hydrogen atoms on the group are optionally substituted with one or more substituents selected from the group consisting of: halogen, trifluoromethyl, C1-C4 alkyl, adamantyl, hydroxyl, amino, nitro, substituted or unsubstituted acetoxy group (AcO), carboxyl, C1-C4 alkoxy, cyano, substituted or unsubstituted phenyl, and —SO$_2$—NH$_2$;

R$_2$ is selected from the group consisting of: H, and methyl, or R$_2$ is none;

R$_3$ is selected from the group consisting of: H, or R$_3$ is none;

R$_4$ is H or methyl;

R$_5$ is selected from the group consisting of: C1-C4 alkyl, C3-C7 cycloalkyl or benzyl, wherein the hydrogen on benzyl can be optionally substituted by one or more substituents selected from the group consisting of: hydroxy, halogen, C1-C4 alkyl, C1-C4 haloalkyl, C1-C4 alkoxy, C1-C4 haloalkoxy, and C2-C4 alkylene; wherein the hydrogen atoms of two adjacent carbons on phenyl are optionally substituted by "—O—(CH$_2$)$_n$O—", wherein n=1, 2 or 3;

n1, n2, and n3 are 1; and/or

X is O or NR$_8$, wherein the R$_8$ is H or methyl.

In another preferred embodiment, R$_1$ is aryl or heteroaryl selected from the group consisting of: phenyl, and benzothiazolyl; in which the hydrogen atoms on the aryl or heteroaryl are optionally substituted with one or more substituents selected from the group consisting of: halogen, trifluoromethyl, C1-C4 alkyl, hydroxyl, amino, nitro, substituted or unsubstituted acetoxy group (AcO), carboxyl, C1-C4 alkoxy, cyano, substituted or unsubstituted phenyl, —SO$_2$—NH$_2$; and/or X is NR$_8$, wherein the R$_8$ is H or methyl.

In another preferred embodiment, R$_5$ is selected from the group consisting of: benzyl, wherein the hydrogen atoms on benzyl can be optionally substituted by one or more substituents selected from the group consisting of: hydroxy, halogen, C1-C4 alkyl, C1-C4 fluoroalkyl, C1-C4 fluoroalkoxy, and C2-C4 alkylene; wherein the hydrogen atoms of two adjacent carbons on phenyl structure of benzyl are optionally substituted by "—O—(CH$_2$)$_n$O—", wherein n=1, 2 or 3.

In another preferred embodiment, the C1-C4 alkyl is deuterated methyl.

In another preferred embodiment, the compound is selected from the group consisting of:

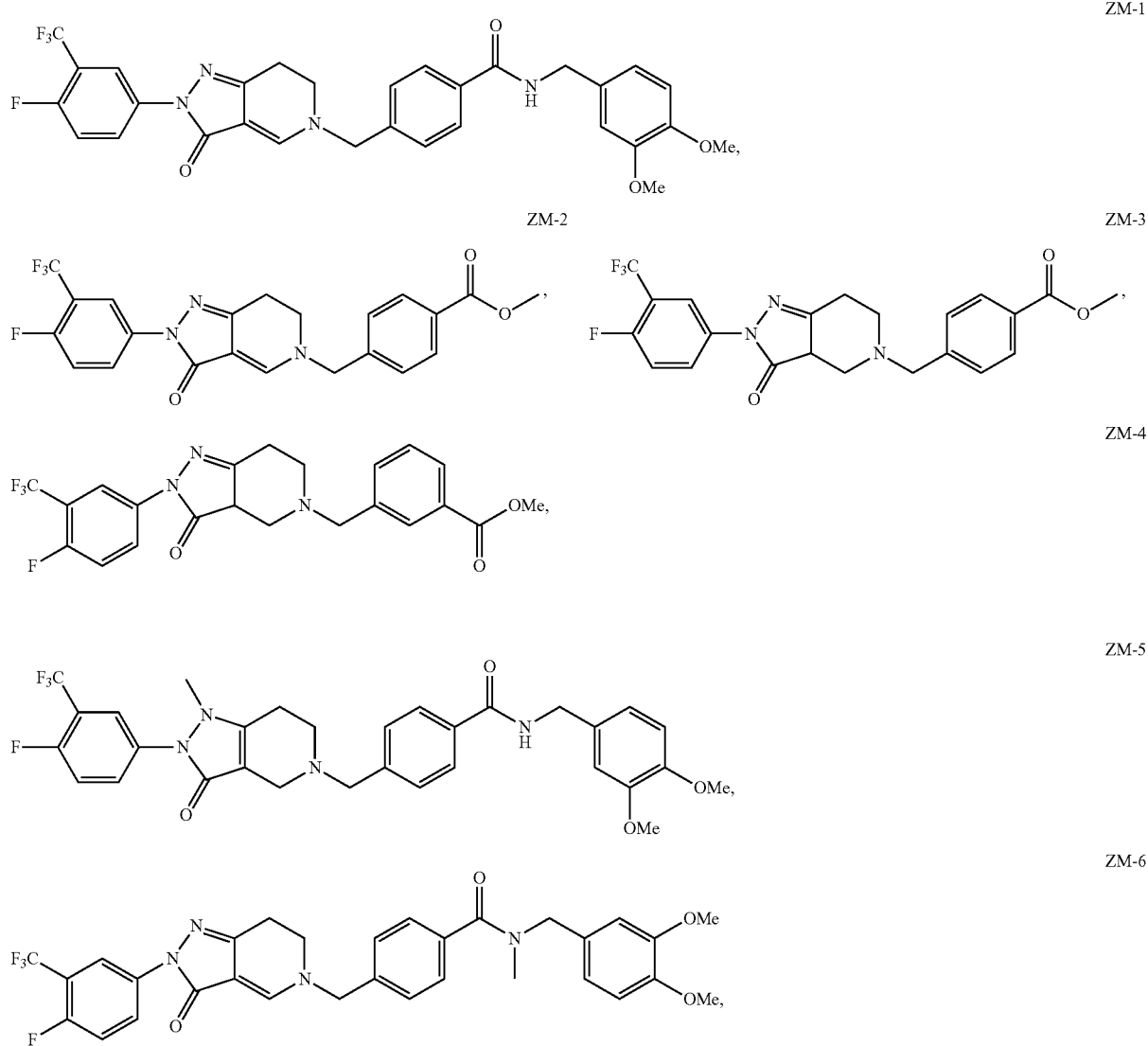

-continued
ZM-7
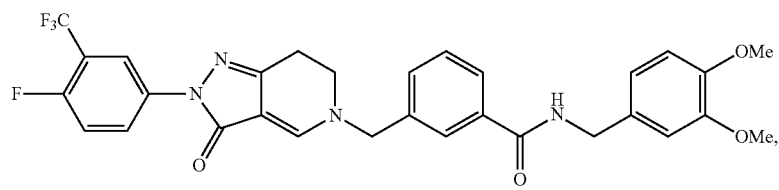
ZM-8
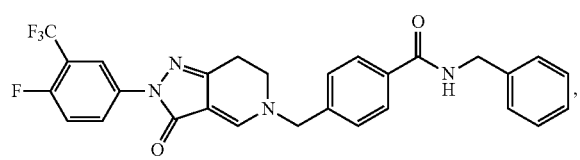
ZM-9
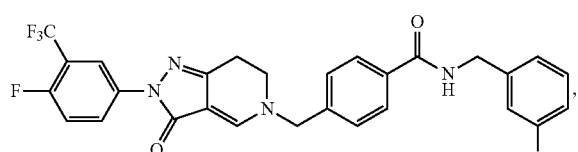
ZM-10
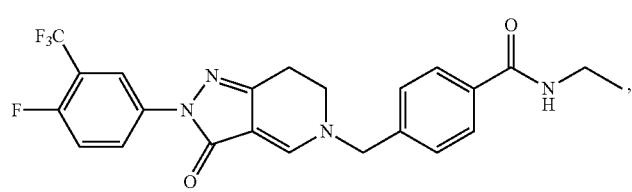
ZM-11
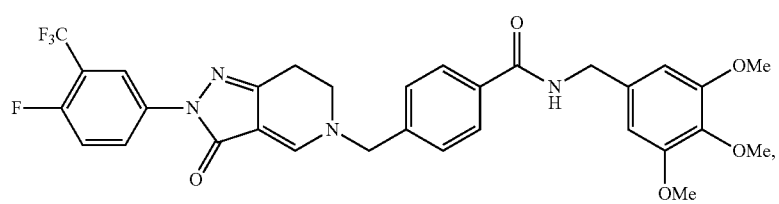
ZM-12
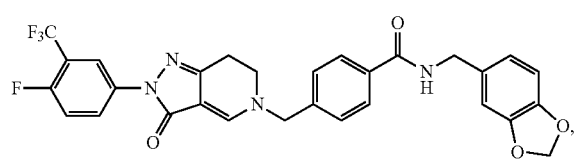
ZM-13
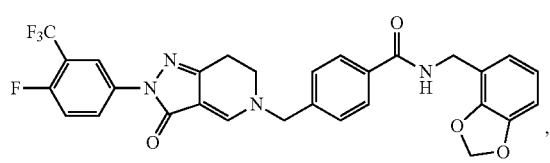
ZM-14
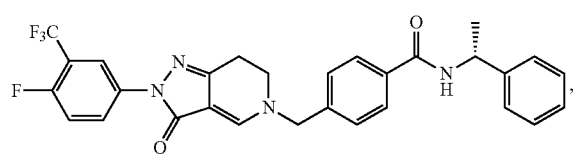
ZM-15
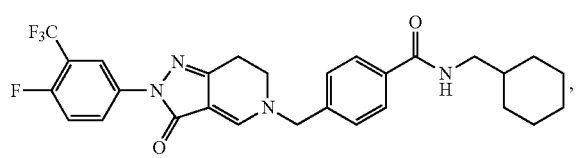
ZM-16
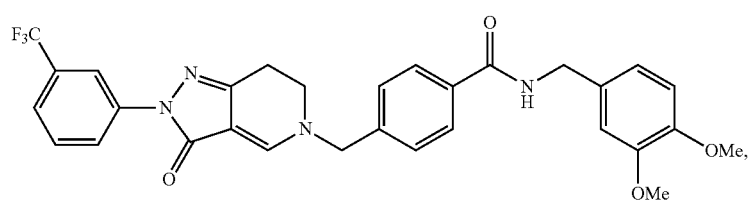
ZM-17
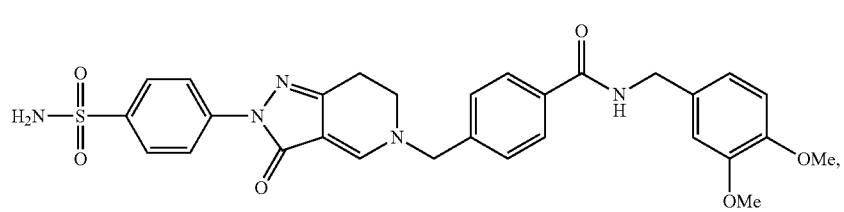

-continued
ZM-18
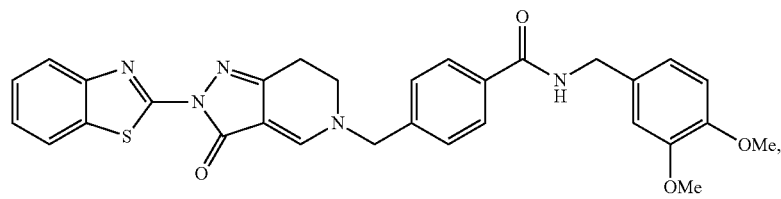
ZM-19
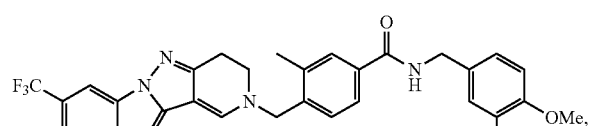
ZM-20
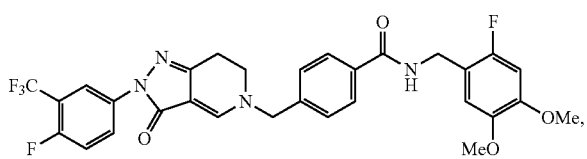
ZM-21
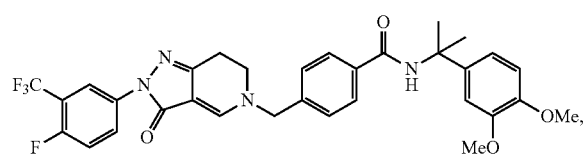
ZM-22
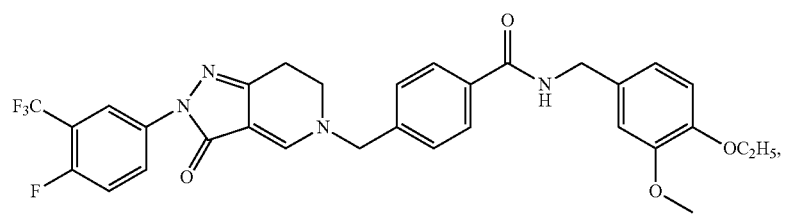
ZM-23
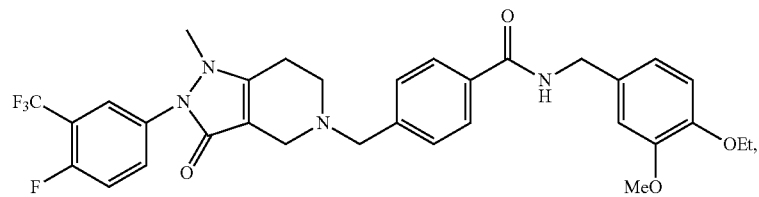
ZM-24
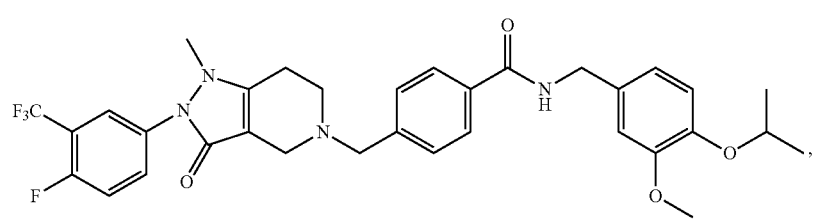
ZM-25
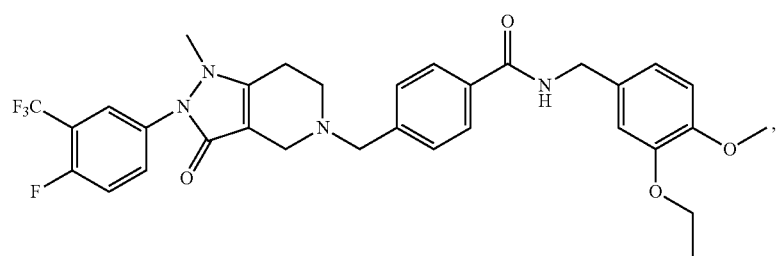
ZM-26

-continued
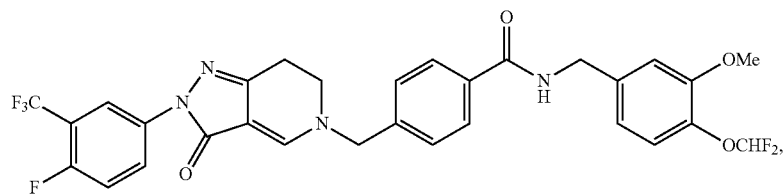
ZM-27
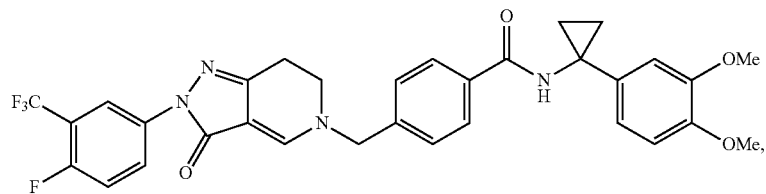
ZM-28
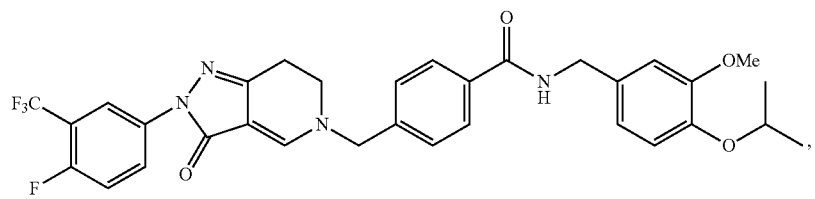
ZM-29
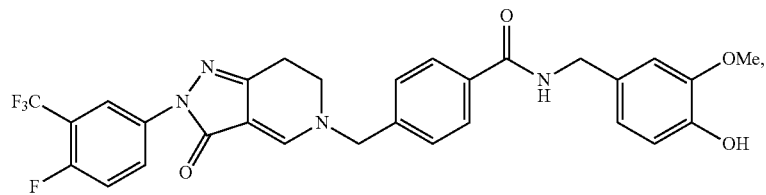
ZM-30
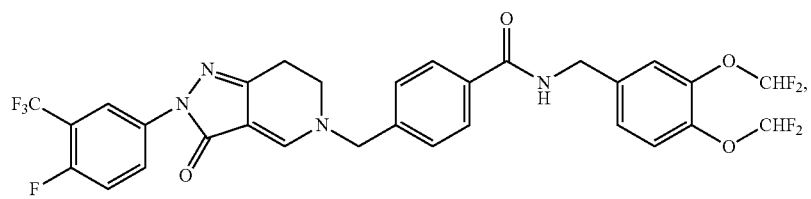
ZM-31
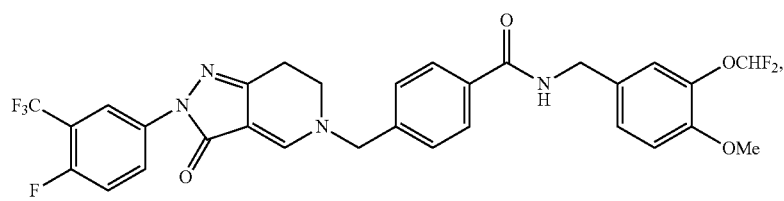
ZM-32
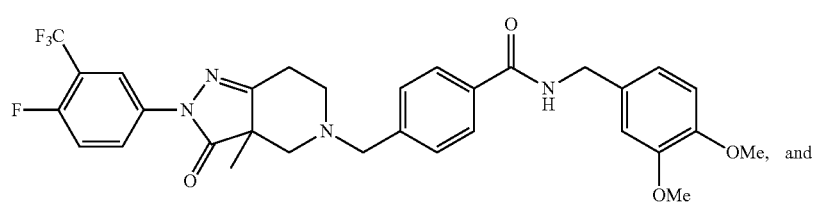
ZM-33
and
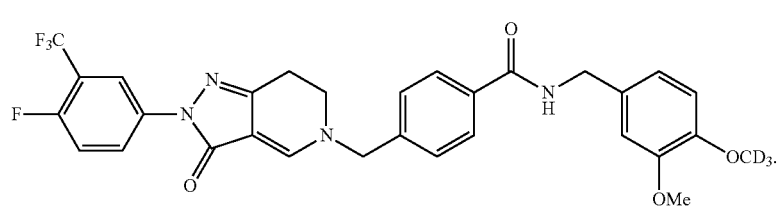
ZM-34

In the second aspect of the present invention, a compound of formula Ia is provided:

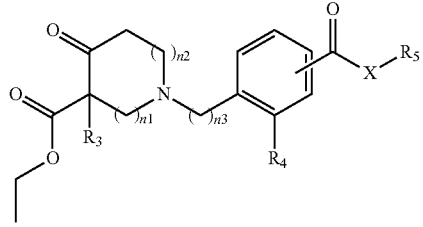

Ia wherein $R_3$, $R_4$, $R_5$, X, n1, n2 and n3 are defined as above.

In the third aspect of the present invention, a preparation method of compound Ia of the second aspect of the present invention is provided, wherein it comprises the following step:

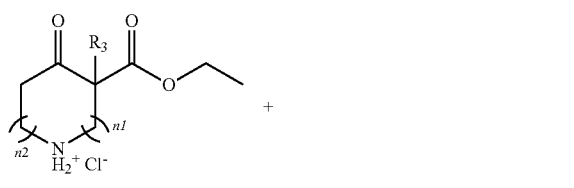

Ia1

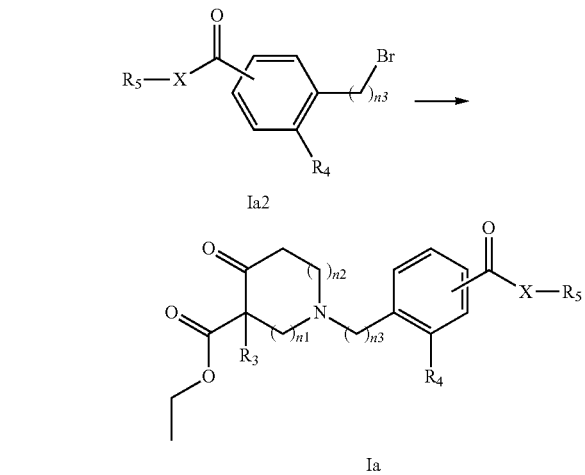

Ia2

Ia in an inert solvent, reacting a compound of formula Ia1 with a compound of formula Ia2, thereby obtaining the compound of formula Ia;

wherein the groups are defined as in the second aspect of the present invention.

In another preferred embodiment, the —X—$R_5$ is —$OCH_3$.

In another preferred embodiment, said reaction is carried out in the presence of a base; and preferably the base is selected from the group consisting of: $K_2CO_3$, $Na_2CO_3$, $Cs_2CO_3$, NaH, and the combinations thereof.

In the fourth aspect of the present invention, a preparation method of compound I of the first aspect of the present invention is provided, which it comprises the following steps:

(1) in an inert solvent, reacting a compound of formula Ia with any of compounds of formula Ib, thereby obtaining a compound of formula

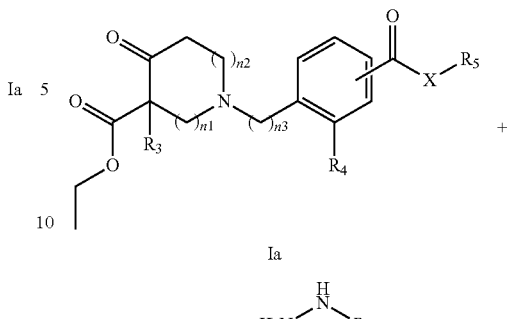

Ia

Ib

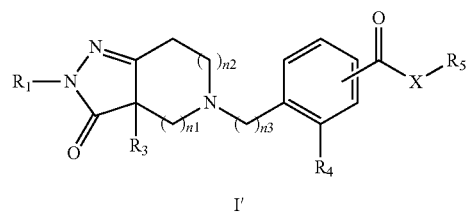

I'

(b1) optionally dehydrogenizing the compound of formula I' in an inert solvent, thereby forming a compound of formula I";

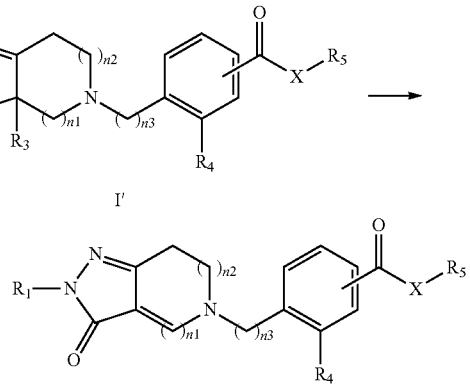

I'

I"

(b2) optionally, in an inert solvent, conducting an elimination reaction with the compound of formula I' and $R_2I$, thereby forming a compound of formula I''':

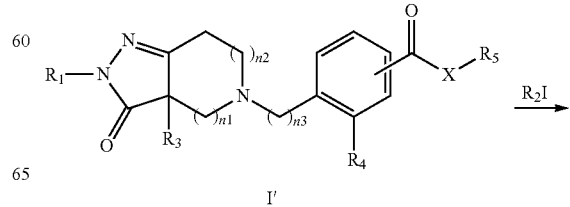

I'

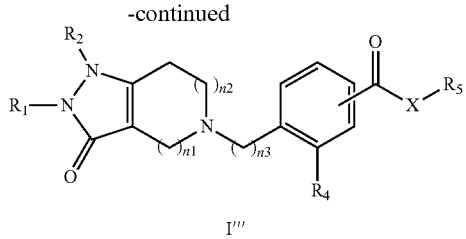

I''' wherein the groups are defined as in the first aspect of the present invention.

In another preferred embodiment, the compound of formula Ia is prepared by the method of the third aspect of the invention.

In another preferred embodiment, in step (2) and step (3), $R_3$ is H.

In another preferred embodiment, step (1) is conducted in the presence of a base, and preferably in the presence of $Et_3N$ and/or EtONa; and more preferably, the EtONa is newly-prepared EtONa.

In another preferred embodiment, in step (2), the dehydrogenation reaction is conducted in the presence of reagent selected from the group consisting of: palladium/carbon, 2,3-dichloro-5,6-dicyano-1,4-benzoquinone, and preferably in the presence of 10% palladium on carbon.

In another preferred embodiment, in step (3), the reaction is carried out in the presence of a base; and preferably, said base is selected from the group consisting of: LDA, $K_2CO_3$, NaOH, and the combinations thereof.

In another preferred embodiment, when the X in formula I', I" or I''' is O, the method optionally comprises the following step:

(i) when $R_5$ is other than H, then in an inert solvent, conducting a hydrolysis reaction of formula Ic compound, thereby forming a compound of formula Id;

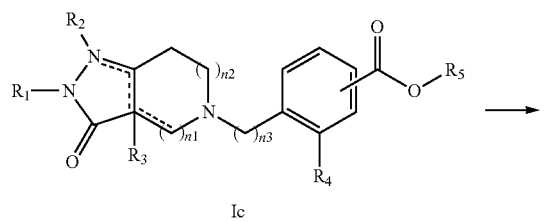

Ic

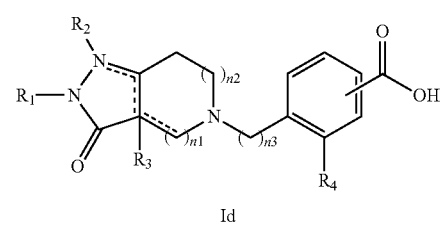

Id (ii) in an inert solvent, reacting the compound of formula Id with $R_5$—$NH_2$, thereby forming a compound of formula Ie:

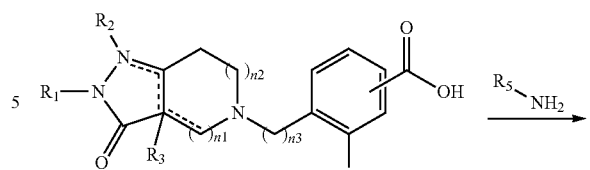

Id

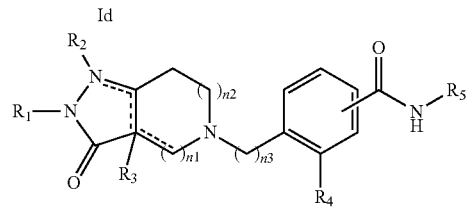

Ie wherein each group is defined as in claim 1.

In another preferred embodiment, in formula Ic and Ie, $R_5$ is same or different.

In another preferred embodiment, step (i) is conducted in the presence of an alkali metal hydroxide; and preferably, the alkali metal hydroxide is selected from the group consisting of: LiOH, NaOH, and the combinations thereof.

In another preferred embodiment, step (i) is conducted in the presence of a condensating agent, and preferably, the condensating agent is selected from the group consisting of: EDCI (1-ethyl-(3-dimethylaminopropyl) carbodiimide hydrochloride), pyridine/EDC/HOBT, DCC, DCC/HOBt, DCC/DMAP, and the combinations thereof.

In the fifth aspect of the present invention, a pharmaceutical composition is provided. wherein it comprises a therapeutically effective amount of compound of formula I, or a pharmaceutically acceptable salt thereof, and a pharmaceutically acceptable carrier.

In another preferred embodiment, the pharmaceutical composition comprises a therapeutically effective amount or a safe and effective amount of a compound of formula I, or a pharmaceutically acceptable salt thereof.

In another preferred embodiment, the pharmaceutical composition comprises 0.0001-99 wt % of the compound of formula I, or a pharmaceutically acceptable salt thereof, and a pharmaceutically acceptable carrier as balance.

In another preferred embodiment, the pharmaceutical composition is used to treat a disease associated with AMPK activity.

In another preferred embodiment, the pharmaceutical composition is used for treatment of glycolipid metabolic disorders; preferably, it is used for treatment of a disease selected from the group consisting of diabetes and obesity.

In the sixth aspect of the present invention, the use of compound of the first aspect of the present invention is provided, wherein it is used for:

(a) preparation of an AMPK activator;
(b) preparation of an AMPK and/or ACC phosphorylation promoter;
(c) in vitro non-therapeutic activation of AMPK activity;
(d) non-therapeutic promotion of AMPK and/or ACC phosphorylation in vitro;
(e) preparation of a pharmaceutical composition for treatment of a disease associated with AMPK kinase activity.

In another preferred embodiment, the activation is dose-dependent activation when it is used for in vitro non-therapeutic activation of AMPK activity.

In another preferred embodiment, the activation is concentration-dependent activation when it is used for in vitro non-therapeutic activation of AMPK activity.

In another preferred embodiment, the activation is molecular level activation or cell-level activation when it is used for in vitro non-therapeutic activation of AMPK activity.

In the seventh aspect of the present invention, an AMPK activity activator is provided, wherein it comprises: an activatingly effective amount of a compound of formula I or a pharmaceutically acceptable salt thereof.

In another preferred embodiment, the activator is a molecular AMPK activator.

In another preferred embodiment, the activator is an intracellular AMPK activator.

In the eighth aspect of the present invention, a method for activation of AMPK activity is provided, wherein it comprises administrating a compound of formula I, or a pharmaceutically acceptable salt thereof.

In the ninth aspect of the present invention, it provided a method for treating a disease relating to AMPK activity, which comprises: administrating a therapeutically effective amount of a compound of Formula I, or a pharmaceutically acceptable salt thereof to a subject in need.

In another preferred embodiment, the subject includes mammal (such as human).

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Figure 1:
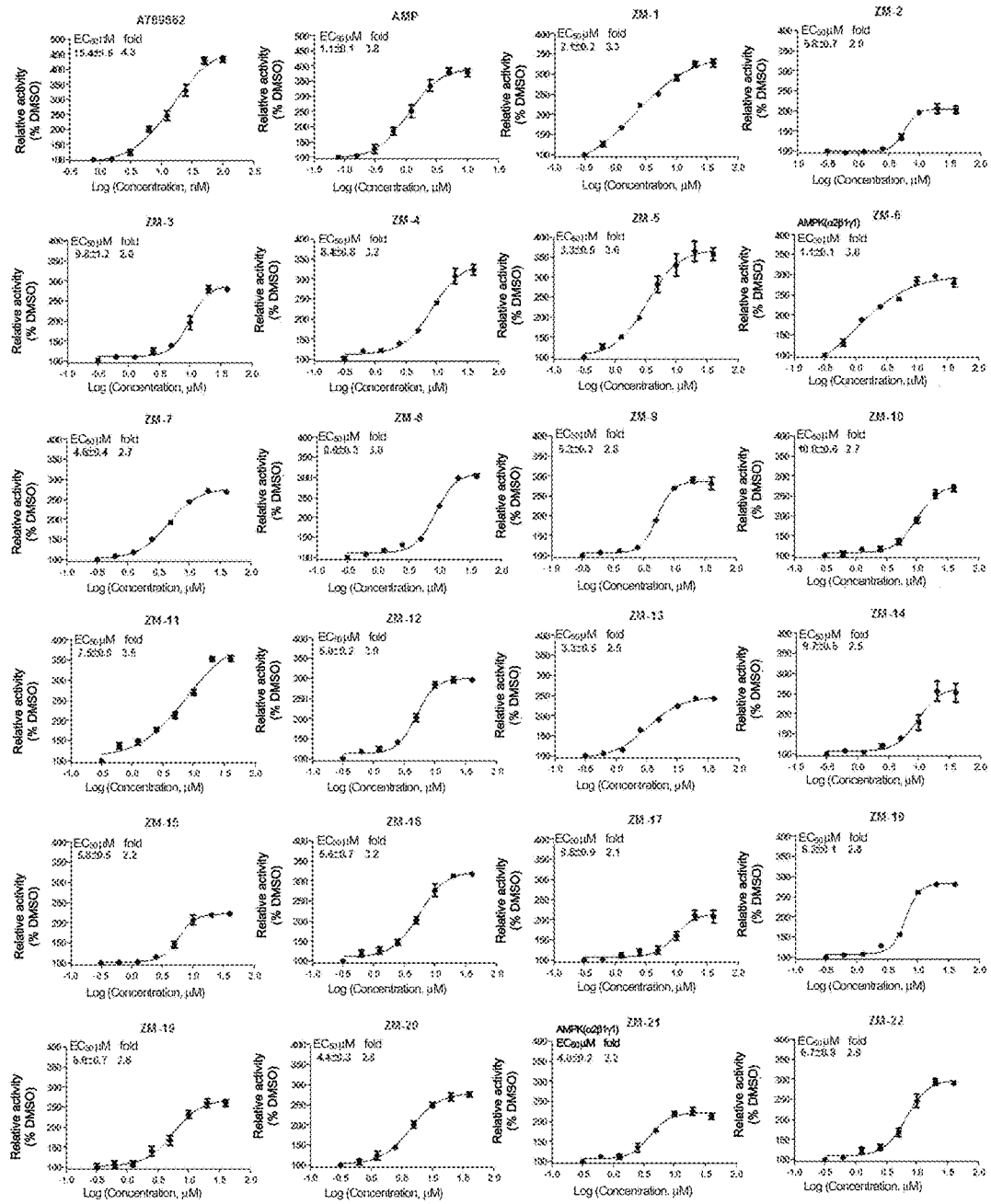
FIG. 1 shows the experimental results of AMPK ($\alpha 2\beta 1\gamma 1$) activation at various molecular levels of various compounds.
Figure 1:
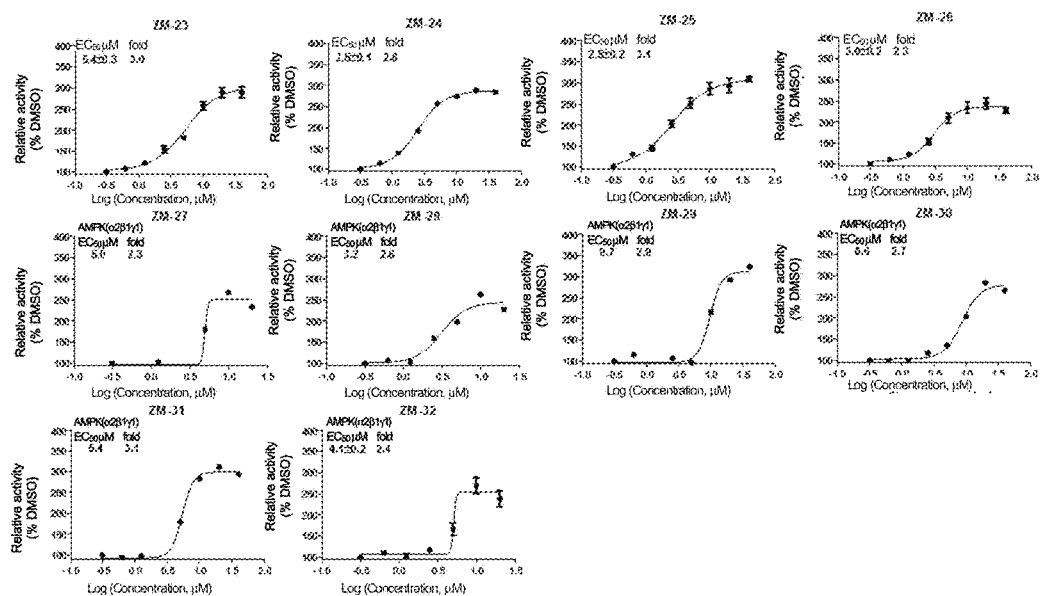

Through long-term and intensive studies, the inventors have prepared a class of pyrazolone compounds which have directly AMPK activation activity and can be used in the preparation of medicines for treating obesity and diabetes. The present invention is completed based on this discovery.

Terms

In the present invention, the alkyl group includes a linear or branched alkyl group; the alkenyl group includes straight or branched alkenyl group; and the alkynyl group includes linear or branched alkynyl group. The halogen is F, Cl, Br or I, and preferably F or Br.

Unless specifically indicated, in the present invention, the term "substitute" or "substituted" refers to one or more hydrogen atoms on the group are substituted by any of the following groups: C1-C4 alkyl group, C3-C7 cycloalkyl group, C1-C4 alkoxy, halogen, hydroxy, carboxy (—COOH), C1-C4 aldehyde group, C2-C4 acyl group, C2-C4 ester group, amino, or phenyl; wherein the phenyl includes unsubstituted phenyl or phenyl substituted by one or more substituents, wherein the substituent is selected from: halogen, C1-C4 alkyl, cyano, OH, nitro, C3-C7 cycloalkyl group, C1-C4 alkoxy, or amino.

In particular, in the present invention, unless otherwise indicated, any atom mentioned includes all isotope forms. For example, when referring to "hydrogen atom", it means hydrogen atom, deuterium atom, tritium atom or any combinations thereof. In the present invention, the abundance of various isotopic atoms of an element may be a state in which the element is naturally occurring in nature, or may be an isotopically enriched state.

As used herein, the term "C1-C4 alkyl" refers to a linear or branched alkyl with 1 to 4 carbon atoms, such as methyl, ethyl, propyl, isopropyl, butyl, isobutyl, sec-butyl, tert-butyl, or similar groups.

Term "C3-C7 cycle alkyl" refers to a cycle alkyl with 3 to 7 carbon atoms, such as cyclopropyl, cyclobutyl, cyclopentyl, cycloheptyl, or the like.

The term "5-10 membered aryl" refers to an aryl with 5 to 10 carbon atoms, such as monocyclic or bicyclic aryl, such as phenyl, naphthyl, or the like.

The term "5-10 membered heteroaryl" refers to a heteroaryl with 5 to 10 carbon atoms or heteroatoms (selected from N, O or S), such as pyrrolyl, pyridyl, furyl, or the like.

The term "C1-C4 alkoxy" refers to a straight or branched chain alkoxy group having 1 to 4 carbon atoms, such as methoxy, ethoxy, propoxy, isopropoxy, butoxy, iso-butoxy, sec-butoxy, tert-butoxy, or the like.

The term "C1-C4 acyl group" refers to a group having a "—CO-alkyl" structure, and preferably a structure of "—CO—C1-C4 alkyl", such as methyl acyl, ethyl acyl, propyl acyl, isopropyl acyl, butyl acyl, isobutyl acyl, sec-butyl acyl, tert-butyl acyl, or the like.

The term "C1-C4 ester group" refers to a group having an alkyl-COO— structure, and preferably a structure of "C1-C4 alkyl-COO—", such as $CH_3COO$—, $C_2H_5COO$—, $C_3H_8COO$—, $(CH_3)_2CHCOO$—, $nC_4H_9COO$—, $tC_4H_9COO$—, or the like.

The term "C2-C10 ester group" refers to a group having a "—COO—C1-C9 alkyl" structure which processes 2-10 carbon atoms, such as $CH_3COO$—, $C_2H_5COO$—, $C_3H_8COO$—, $(CH_3)_2CHCOO$—, $nC_4H_9COO$—, $tC_4H_9COO$—, or the like.

The term "halogen" refers to F, Cl, Br and I.

In this context, the abbreviations for each compound are as follows:

| EDCI | (1-ethyl-(3-dimethylaminopropyl) carbodiimide hydrochloride) | EDCI | 1-(3-dimethylaminopropyl)-3-ethylcarbodiimide hydrochloride |
|---|---|---|---|
| HOBT | 1-hydroxybenzotriazole | DCC | dicyclohexylcarbodiimide |
| DMAP | 4-dimethylaminopyridine | AMPK | adenosine monophosphate activated protein kinase |
| ACC | Coenzyme A carboxylase | LDA | lithium diisopropylamide |

Compound of Formula I

The present invention provides a compound of formula I:

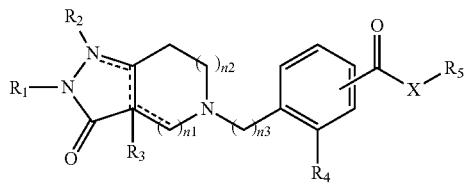

wherein $R_1$ is selected from the group consisting of: H, C1-C4 alkyl, 6- to 12-membered aryl group or 5-10 membered heteroaryl in which the hydrogen atoms on the group are optionally substituted with one or more substituents selected from the group consisting of: halogen, C1-C4 alkyl, C1 to C4 halogen substituted alkyl, adamantyl, hydroxyl, amino, nitro, substituted or unsubstituted acetoxy group (AcO), carboxyl, C1-C4 alkoxy, C1-C4 haloalkoxy, cyano, substituted or unsubstituted phenyl, and —$SO_2$—$NH_2$; wherein the term "substituted" refers to that one or more hydrogen atoms on a group are substituted with substituents selected from the group consisting of: halogen, trifluoromethyl, hydroxy, amino, C1-C4 alkyl, C1-C4 alkoxy, adamantyl, and cyano;

$R_2$ is selected from the group consisting of: H and C1-C4 alkyl, or $R_2$ is none;

$R_3$ is selected from the group consisting of: H and C1-C4 alkyl, or $R_3$ is none;

$R_4$ is selected from the group consisting of: H, C1-C4 alkyl, C1-C4 haloalkyl, halogen, hydroxy, amino, nitro, AcO, carboxyl, C1-C4 alkoxy, and cyano;

$R_5$ is selected from the group consisting of: H, C1-C4 alkyl, C3-C7 cycloalkyl, phenyl, and C1-C4 alkylene phenyl, wherein the hydrogen atoms on phenyl or C1-C4 alkylene phenyl can be optionally substituted by one or more substituents selected from the group consisting of: hydroxy, halogen, C1-C4 alkyl, C1-C4 haloalkyl, C3-C7 cycloalkyl, C1-C4 alkoxy, and C1-C4 haloalkoxy; wherein when R5 is a phenyl-containing group, the hydrogen atoms of two adjacent carbons on the phenyl are optionally substituted by "—O—$(CH_2)_n$O—", wherein n=1, 2 or 3;

n1 is 0, 1, or 2;
n2 is 0, 1, 2, or 3;
n3 is 0, 1, or 2;

X is selected from the group consisting of: O and $NR_8$, wherein $R_8$ is selected from the group consisting of: H, C1-C4 alkyl, C1-C4 haloalkyl, C3-C7 cycloalkyl, phenyl, and C1-C4 alkylene phenyl;

a dashed line is a chemical bond or none.

In another preferred embodiment, the C1-C4 haloalkyl group comprises C1-C4 fluoro group, and preferably trifluoromethyl group.

In another preferred embodiment, $R_1$ is phenyl substituted with 1 to 5 substituents selected from the group consisting of halogen and trifluoromethyl.

In another preferred embodiment, the 6- to 12-membered aryl is phenyl or naphthyl.

In another preferred embodiment, the C1-C4 alkylene phenyl group includes benzyl, —C (cyclopropyl)-phenyl. In another preferred embodiment, $R_1$ is selected from the group consisting of: 6- to 12-membered aryl group or 5-10 membered heteroaryl group in which the hydrogen atoms on the group are optionally substituted with one or more substituents selected from the group consisting of: halogen, trifluoromethyl, C1-C4 alkyl, adamantyl, hydroxyl, amino, nitro, substituted or unsubstituted acetoxy group (AcO), carboxyl, C1-C4 alkoxy, cyano, substituted or unsubstituted phenyl, and —$SO_2$—$NH_2$;

$R_2$ is selected from the group consisting of: H and methyl, or $R_2$ is none;

$R_3$ is selected from the group consisting of: H, or $R_3$ is none;

$R_4$ is H or methyl;

$R_5$ is selected from the group consisting of: C1-C4 alkyl, C3-C7 cycloalkyl or benzyl, wherein the hydrogen atoms on benzyl can be optionally substituted by one or more substituents selected from the group consisting of: hydroxy, halogen, C1-C4 alkyl, C1-C4 haloalkyl, C1-C4 alkoxy, C1-C4 haloalkoxy, and C2-C4 alkylene; wherein the hydrogen atoms of two adjacent carbons on phenyl are optionally substituted by "—O—$(CH_2)_n$O—", wherein n=1, 2 or 3;

n1, n2, n3 are 1;

X is O or $NR_8$, wherein the $R_8$ is H or methyl; and a dashed line ($\cdots$) is a chemical bond or none.

In another preferred embodiment, $R_1$ is aryl or heteroaryl selected from the group consisting of: phenyl, and benzothiazolyl; wherein the hydrogen atoms on the aryl or heteroaryl are optionally substituted with one or more substituents selected from the group consisting of: halogen, trifluoromethyl, C1-C4 alkyl, hydroxyl, amino, nitro, substituted or unsubstituted acetoxy group (AcO), carboxyl, C1-C4 alkoxy, cyano, substituted or unsubstituted phenyl, and —$SO_2$—$NH_2$; and/or X is $NR_8$, wherein $R_8$ is H or methyl.

In preferred compounds with superior activity, $R_5$ is selected from benzyl, wherein the hydrogen on benzyl can be optionally substituted by one or more substituents selected from the group consisting of: hydroxy, halogen, C1-C4 alkyl, C1-C4 fluoroalkyl, C1-C4 fluoroalkoxy, or C2-C4 alkylene; wherein the hydrogen atoms of two adjacent carbons on phenyl structure of benzyl are optionally substituted by "—O—$(CH_2)_n$O—", wherein n=1, 2 or 3.

In another preferred embodiment, the compound is selected from the group consisting of:

ZM-1

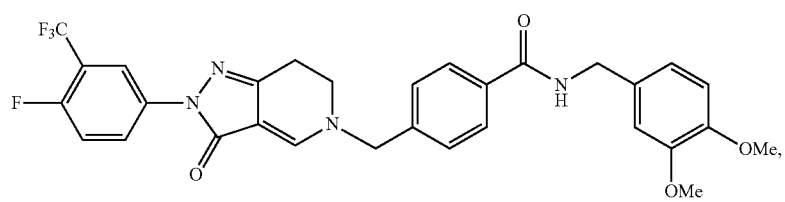

-continued
ZM-2
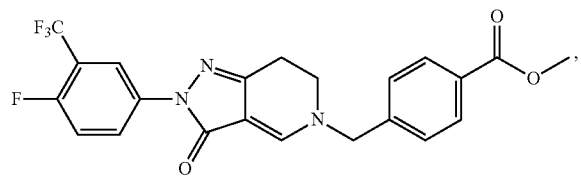
ZM-3
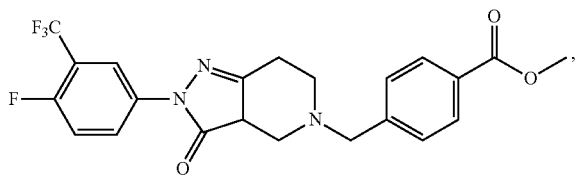
ZM-4
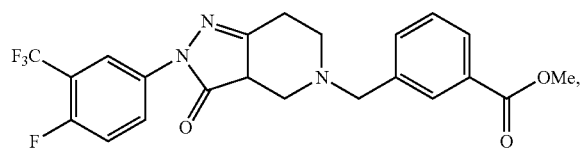
ZM-5
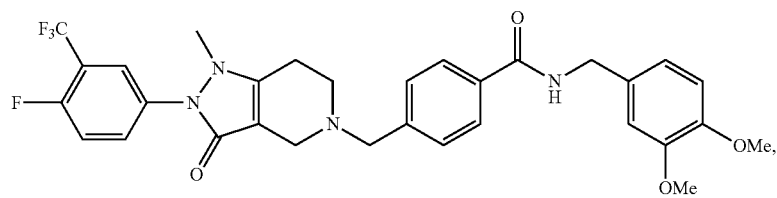
ZM-6
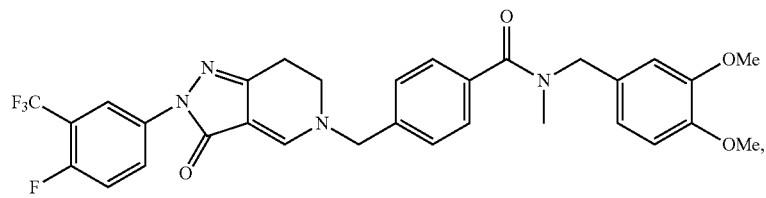
ZM-7
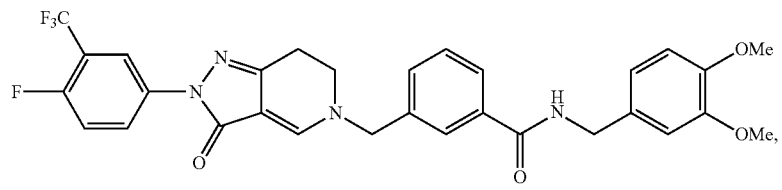
ZM-8
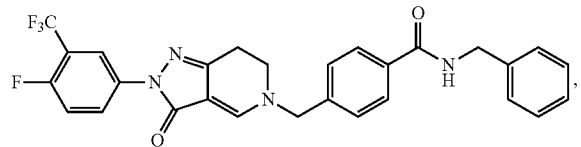
ZM-9
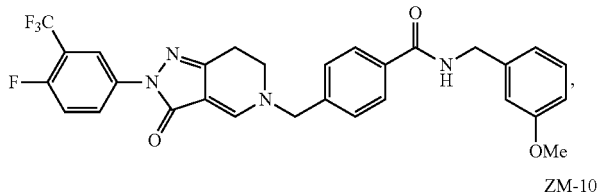
ZM-10
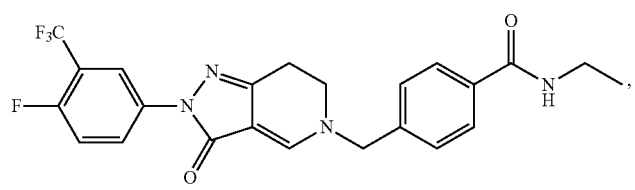
ZM-11
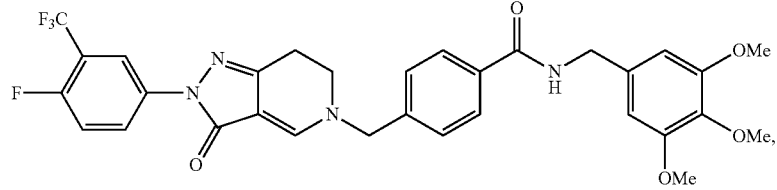

-continued
ZM-12
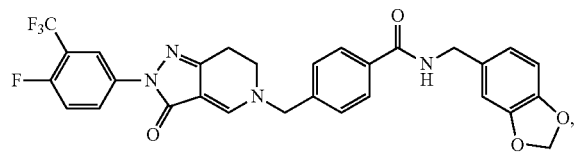
ZM-13
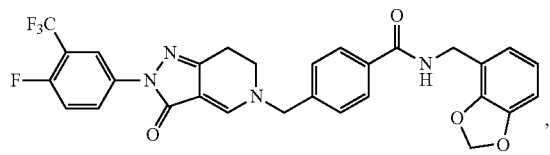
ZM-14
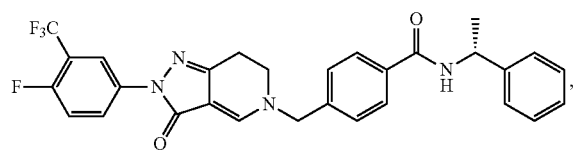
ZM-15
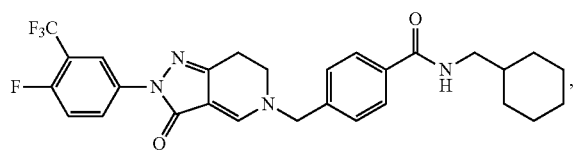
ZM-16
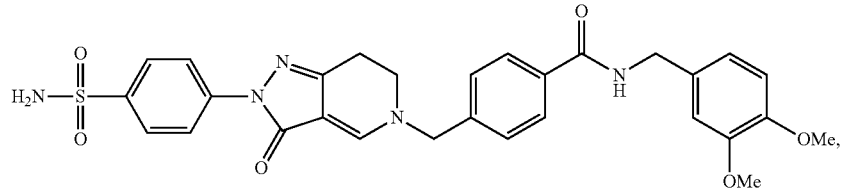
ZM-17
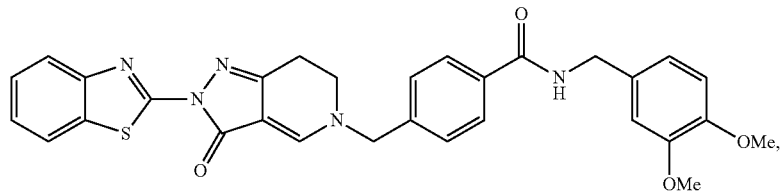
ZM-18
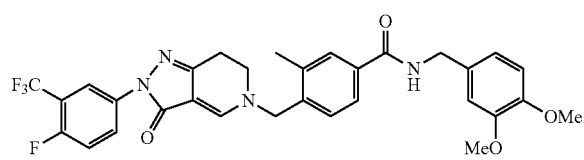
ZM-19
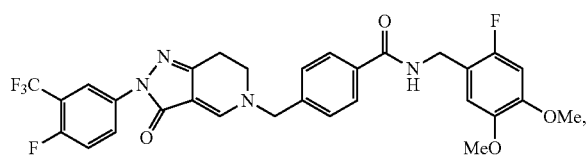
ZM-20
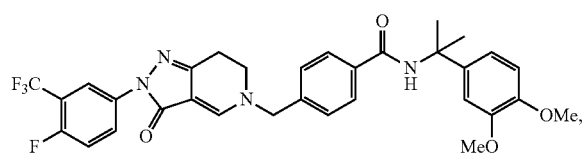
ZM-21
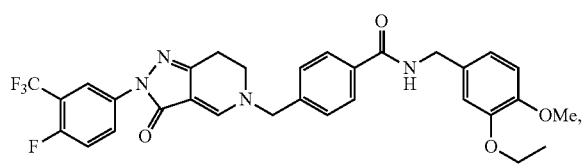
ZM-22
ZM-23
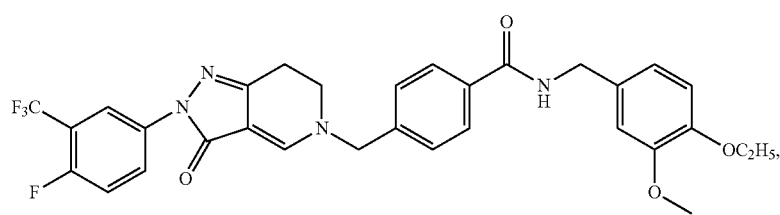

-continued
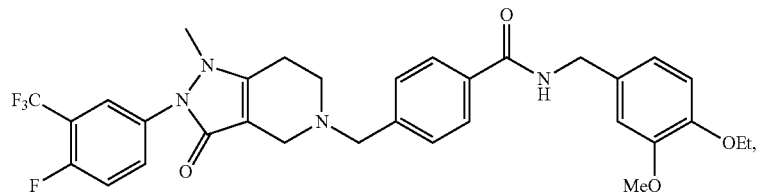
ZM-24
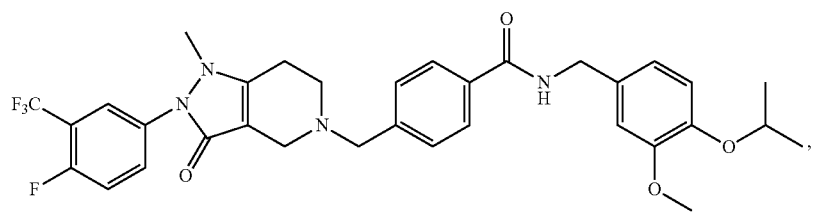
ZM-25
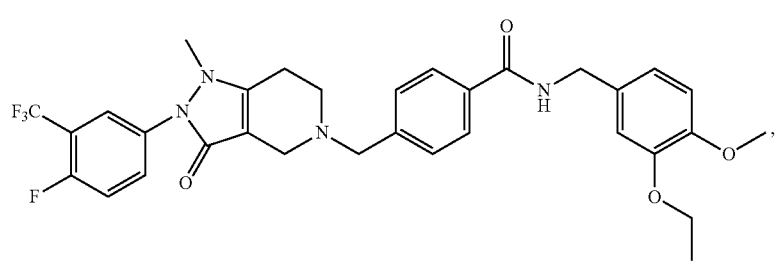
ZM-26
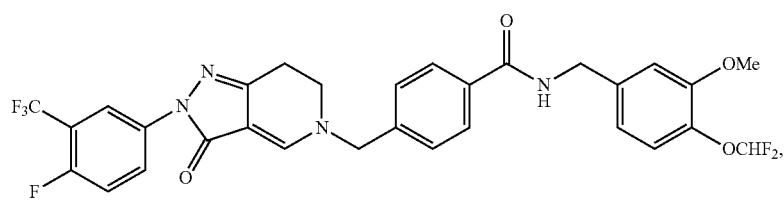
ZM-27
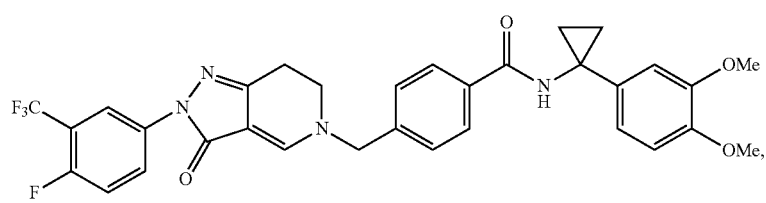
ZM-28
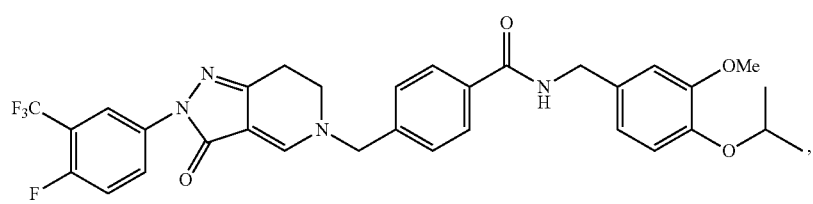
ZM-29
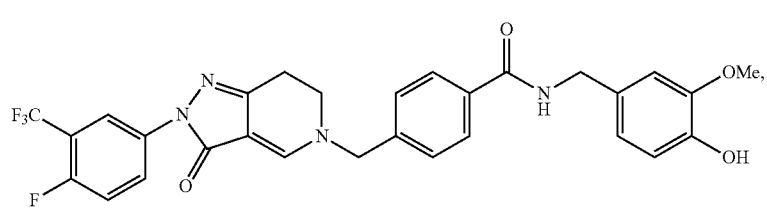
ZM-30

ZM-31
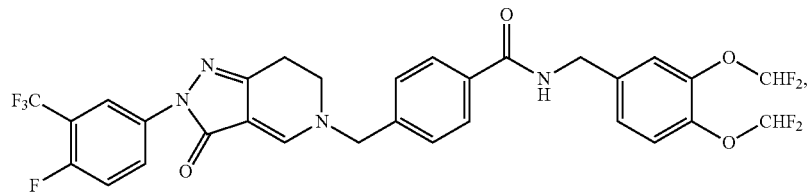

ZM-32
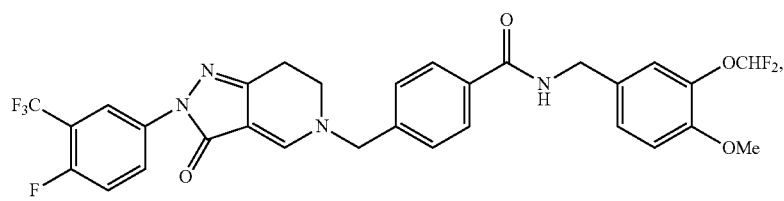

ZM-33
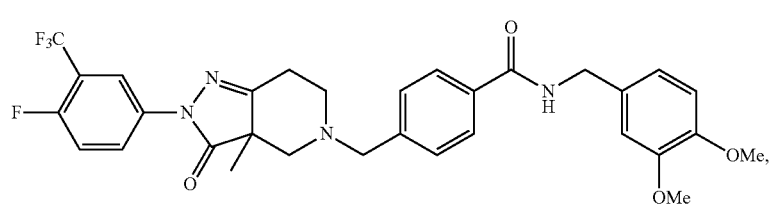

ZM-34
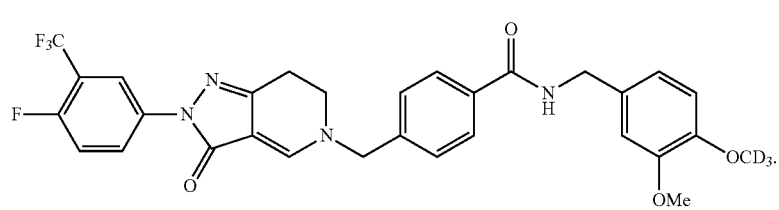

Preparation of Compound of Formula I

The invention further provides a preparation method of compound of formula I, wherein it comprises the following steps:

(1) in an inert solvent, reacting a compound of formula Ia with any of compound of formula Ib, thus obtaining a compound of formula I':

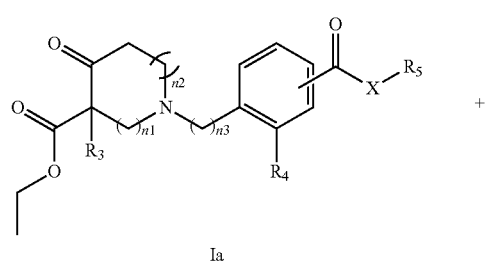

Ia

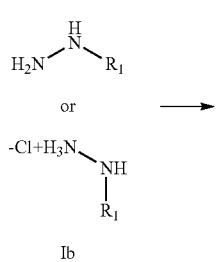

Ib

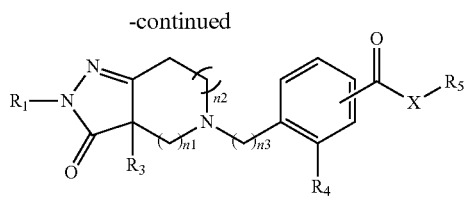

I'

(b1) optionally dehydrogenizing the compound of formula I' in an inert solvent, thereby forming a compound of formula I":

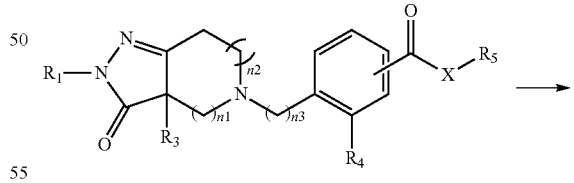

I'

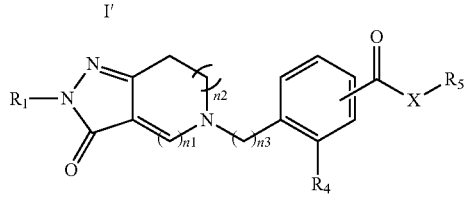

I"

(b2) optionally, in an inert solvent, conducting an elimination reaction with compound of formula I' and $R_2I$, thereby forming a compound of formula I''';

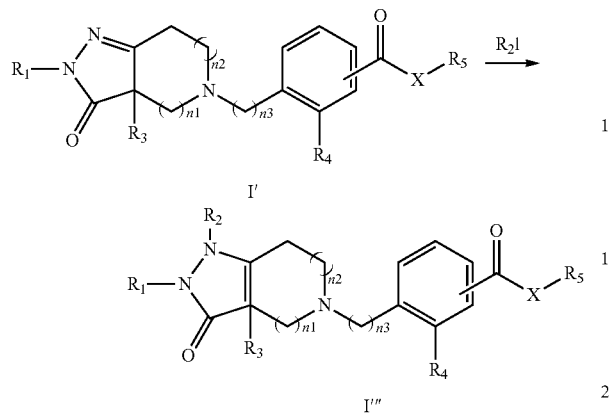

I'

I''' wherein the groups are defined as above.

In another preferred embodiment, in step (2) and step (3), $R_3$ is H.

In another preferred embodiment, step (1) is conducted in the presence of a base, and preferably in the presence of $Et_3N$ and/or EtONa; and more preferably, the EtONa is newly-prepared EtONa.

In another preferred embodiment, in step (2), the dehydrogenation reaction is conducted in the presence of reagent selected from the group consisting of: palladium/carbon, 2,3-dichloro-5,6-dicyano 4-benzoquinone, and preferably in the presence of 10% palladium on carbon.

In another preferred embodiment, in step (3), said reaction is carried out in the presence of a base; and preferably the base is selected from the group consisting of: LDA, $K_2CO_3$, NaOH, and the combinations thereof.

When the X in formula I', I'' or I''' is O, the method further optionally comprises the following steps:

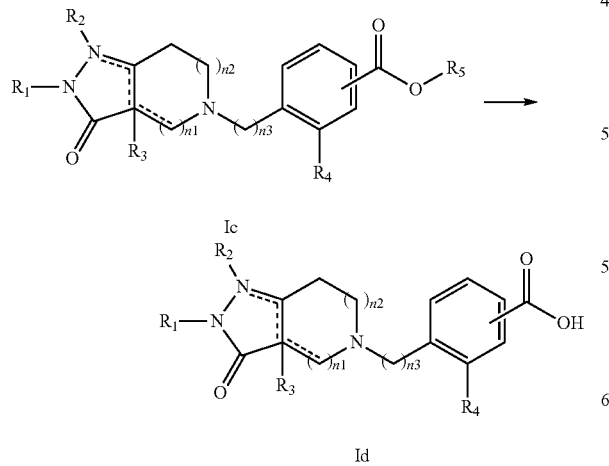

Ic

Id (i) In an inert solvent, conducting a hydrolysis reaction of a compound of formula Ic, thereby forming a compound of formula Id;

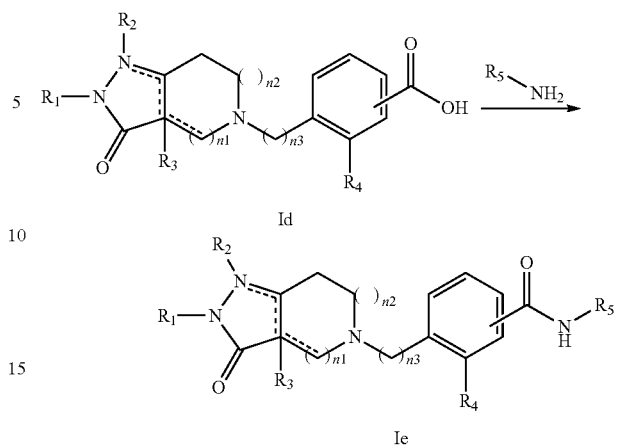

Id

Ie (ii) in an inert solvent, reacting the compound of formula Id with $R_5$—$NH_2$, thus obtaining a compound of formula Ie;

wherein the groups are defined as above; and the $R_5$ in formula Ic and Ie can be same or different.

In another preferred embodiment, step (i) is conducted in the presence of an alkali metal hydroxide, and preferably, the alkali metal hydroxide is selected from the group consisting of: LiOH, NaOH, and the combinations thereof.

In another preferred embodiment, step (i) is conducted in the presence of a condensating agent and preferably, the condensating agent is selected from the group consisting of: EDCI (1-ethyl-(3-dimethylaminopropyl) carbodiimide hydrochloride), pyridine/EDC/HOBT, DCC, DCC/HOBt, DCC/DMAP, and the combinations thereof.

Each of the starting materials may be prepared by methods known in the art, or is commercially available. In a preferred embodiment, the compound of formula Ia is prepared by the following method:

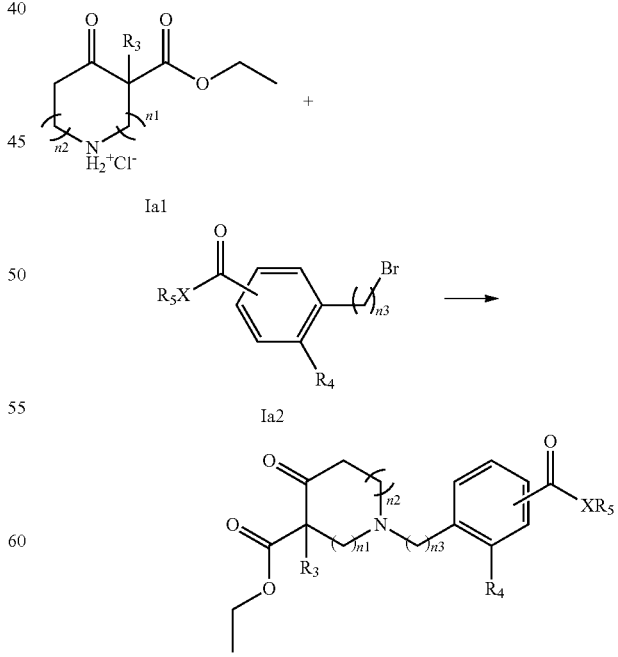

Ia1

Ia2

Ia in an inert solvent, reacting a compound of formula Ia1 and a compound of formula Ia2, thereby forming formula Ia compound.

In another preferred embodiment, the reaction is carried out in the presence of a base; and preferably the base is selected from the group consisting of: $K_2CO_3$, $Na_2CO_3$, $Cs_2CO_3$, NaH, and the combinations thereof.

One preferred method for preparing a compound of formula I comprises the following steps:

react with the corresponding amines in the presence of a condensing agent such as EDCI (1-ethyl-(3-dimethylamino-propyl) carbodiimide hydrochloride), thereby forming a compound of formula I.

In the above reaction formulas, each of the groups is defined as above.

Use of Compound of Formula I

The present invention also provides the use of compound of formula I.

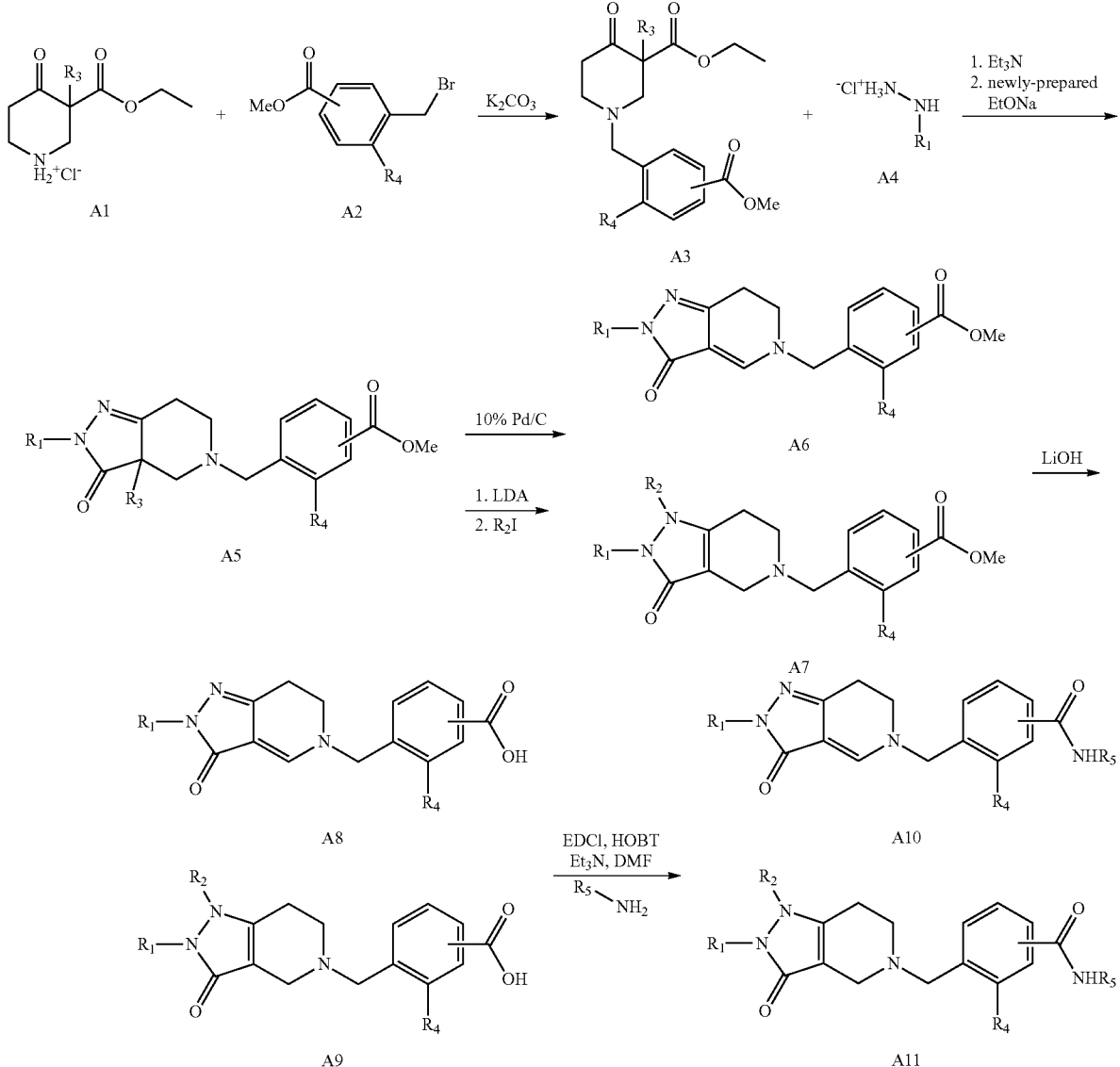

In particular, a substituted 3-ethoxycarbonyl-4-piperidone hydrochloride A1 is condensed with a substituted benzyl bromide (A2) by using basic potassium carbonate, thereby forming an intermediate A3. The substituted aryl hydrazine or its hydrochloride salt (A4) is reacted with the piperidone intermediate A3 to form pyrazolone compound A5. When $R_3$ is H, the compound A5 is dehydrogenated with 10% Pd/C to give a double bond compound A6. When $R_3$ is H, compound A5 is reacted with base LDA and the corresponding alkyl iodide, thereby forming compound A7. Compounds A6 and A7 are hydrolyzed to form the corresponding acids which In a preferred embodiment of the present invention, the compound of formula I is used to prepare an AMPK activator, wherein the AMPK activator comprises: an activatingly effective compound of formula I or a pharmaceutically acceptable salt thereof. The activator may be a molecular AMPK activator or an intracellular AMPK activator.

In a preferred embodiment of the present invention, the compound of formula I is used to prepare an AMPK and/or ACC phosphorylation promoter.

In a preferred embodiment of the present invention, the compound of formula I is used to non-therapeutically activate AMPK activity in vitro. The activation is dose-dependent activation or concentration-dependent activation when it is used for in vitro non-therapeutic activation of AMPK activity. In another preferred embodiment, the activation is molecular level activation or cell-level activation when it is used for in vitro non-therapeutic activation of AMPK activity.

In another preferred embodiment, the compound of formula I is used to non-therapeutically promoting AMPK and/or ACC phosphorylation in vitro.

In another preferred embodiment, the pharmaceutical composition is used to prepare a pharmaceutical composition for treatment of a disease associated with AMPK activity. In another preferred embodiment, the pharmaceutical composition is for treatment of a glycolipid metabolic disorder, preferably for treatment of a disease selected from the group consisting of diabetes and obesity.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

COMPOUND PREPARATIVE EXAMPLES

In the following preparative examples, the NMR was measured by a Mercury-Vx 300M instrument manufactured by Varian with NMR calibration: δ H 7.26 ppm (CDCl$_3$). Mass spectrometry was performed on an Agilent 1200 Quadrupole LC/MS. The reagents were mainly supplied by Shanghai Chemical Reagent Company. TLC thin layer chromatography silica gel plate was produced by the Shandong Yantai Huiyou Silicone Development Co., Ltd., model HSGF 254. Normal phase column chromatography silica gel used in the compounds purification was produced by the Qingdao Marine Chemical Factory (sub factory) (model zcx-11, 200-300 mesh).

Preparation Example 1 Methyl 4-((2-(4-fluoro-3-(trifluoromethyl)phenyl)-3-oxo-3a,4,6,7-tetrahydro-2H-pyrazolo[4,3-c]pyridin-5 (3H)-yl)methyl)benzoic acid (1) Ethyl 1-(4-(methoxycarbonyl)benzyl)-4-piperidone-3-carboxylic acid

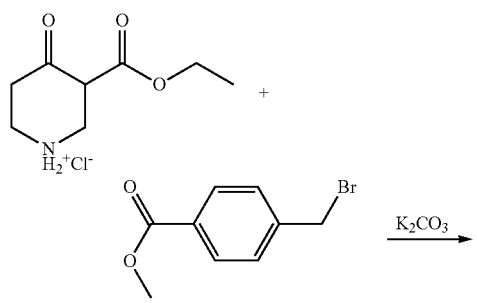

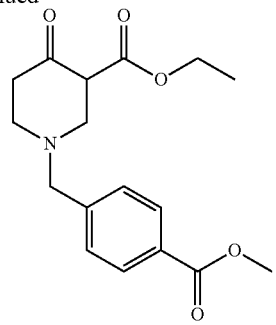

B10

97 mg of 3-ethoxycarbonyl-4-piperidone hydrochloride (0.467 mmol) and 96.3 mg of methyl 4-bromomethylbenzoate (0.420 mmol) were added into a reaction flask and dissolved in acetonitrile. 64.4 mg of K$_2$CO$_3$ (0.467 mmol) was added and reacted overnight at room temperature. The reaction was complete by monitoring with TLC. Acetonitrile was removed under reduced pressure. After it was solved in water, the mixture was extracted three times with ethyl acetate. The organic phase was washed with saturated brine, dried over anhydrous Na$_2$SO$_4$, and the solvent was spin dried under reduced pressure. The residue was purified by column chromatography on silica gel eluting with PE:EA=5:1 to give compound B10, as white solid, 119 mg, yield 89%.

$^1$H NMR (300 MHz, CDCl$_3$) δ 8.01 (dd, J=8.4, 1.8 Hz, 2H), 7.43 (d, J=8.4 Hz, 2H), 4.20 (q, J=7.2 Hz, 2H), 3.91 (s, 3H), 3.68 (s, 2H), 3.19 (s, 1H), 2.60 (t, J=6.0 Hz, 2H), 2.40 (t, J=6.0 Hz, 2H), 1.26 ppm (td, J=7.2, 1.8 Hz, 3H).

(2) Methyl 4-((2-(4-fluoro-3-(trifluoromethyl)phenyl)-3-oxo-3a,4,6,7-tetrahydro-2H-pyrazolo[4,3-c]pyridin-5(3H)-yl)methyl)benzoic acid

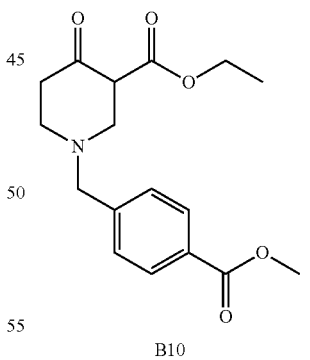

B10

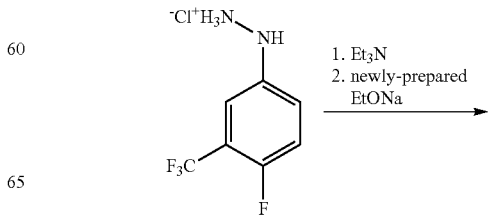

1. Et$_3$N
2. newly-prepared EtONa

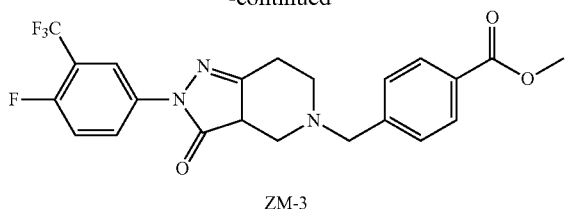

ZM-3

Compound B10 (10.9 g, 34 mmol) and 3-trifluoromethyl-4-fluorophenyl hydrazine hydrochloride (8.21 g, 35.7 mmol) were dissolved in 180 mL of methanol. Triethylamine (5 mL, 35.7 mmol) was added. The mixture was heated to 60° C., reacted for 1 h, and TLC monitored the raw material B10 was reacted completely. The heating was stopped and the mixture was cooled to room temperature, and freshly prepared sodium methoxide (68 mmol, 60 mL) in methanol solution was added, and the mixture was stirred overnight at room temperature. The next day, the reaction mixture was poured slowly into 700 mL 5% citric acid solution, and the precipitated solid was filtered and washed with water for three times. The solid was collected and dried in vacuo with CaCl₂ to give compound ZM-3, as brown solid, 13.5 g. (The compound contained colored impurities and was recrystallized from a methanol/water system to provide a white solid, 85% yield).

¹H NMR (300 MHz, CDCl₃) δ 8.20-8.08 (m, 2H), 8.03 (d, J=8.1 Hz, 2H), 7.42 (d, J=8.1 Hz, 2H), 7.24-7.15 (m, 1H), 3.93 (s, 3H), 3.74 (s, 2H), 3.62-3.49 (m, 2H), 3.31-3.17 (m, 1H), 2.81-2.53 (m, 2H), 2.35-2.16 ppm (m, 2H).

Preparation Example 2 Methyl 4-((2-(4-fluoro-3-(trifluoromethyl)phenyl)-3-oxo-6,7-dihydro-2H-pyrazolo[4,3-c]pyridin-5(3H)-yl)methyl)benzoic acid

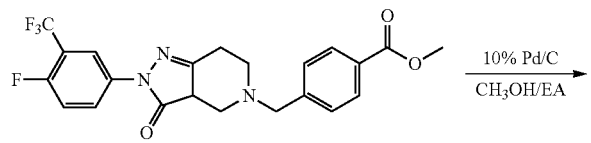

ZM-3

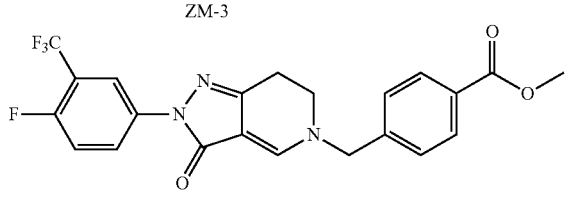

ZM-2

Compound ZM-3 (13 g, 28.9 mmol) was suspended in 500 mL of methanol and 150 mL of ethyl acetate, 10% Pd/C (7 g) was added and the mixture was stirred at room temperature overnight. On next day, TLC monitored that the starting materials were entirely reacted. The mixture was filtered through celite pad, and solid was repeatedly washed methylene chloride/methanol=1/1 solution. The filtrates were combined and concentrated to about 100 mL so that precipitated solid was formed. The precipitated solid was filtered to give a yellow solid, which was washed with a small amount of DCM to give a yellow solid ZM-2 (6.5 g, yield 50%).

¹H NMR (300 MHz, CDCl₃) δ 8.24-8.20 (m, 2H), 8.11 (d, J=7.8 Hz, 2H), 7.98 (s, 1H), 7.42 (d, J=7.8 Hz, 2H), 7.20-7.15 (m, 1H), 4.65 (s, 2H), 3.94 (s, 3H), 3.55-3.50 (t, 2H), 2.92-2.97 ppm (t, 2H).

Preparation Example 3 N-(3,4-dimethoxybenzyl-4-((2-(4-fluoro-3-(trifluoromethyl)phenyl)-3-oxo-6,7-dihydro-2H-pyrazolo[4,3-c]pyridin-5(3H)-yl)methyl)benzamide (1) 4-((2-(4-fluoro-3-(trifluoromethyl)phenyl)-3-oxo-6,7-dihydro-2H-pyrazolo[4,3-c]pyridin-5(3H)-yl)methyl)benzoic acid

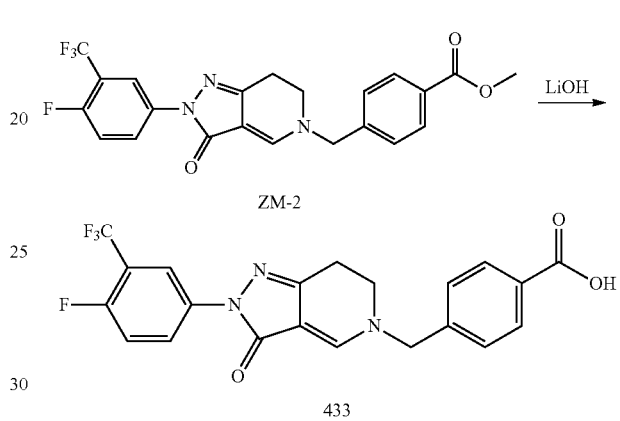

Compound ZM-2 (7.1 g, 15.8 mmol) was suspended in 250 mL, and aqueous solution of LiOH (1.33 g, 31.6 mmol) 120 mL was added, and the mixture was stirred at room temperature overnight. On next day, the solution was clarified, TLC monitored that the starting materials were entirely reacted. Most of methanol was removed in vacuum under reduced pressure, and 1N HCl solution was added to adjust pH to 1-2, and the solid was precipitated, and vacuum filtrated to collect solid. The solid was washed with water for 3 times, dried in vacuo to give a white solid (6.4 g, 90% yield).

(2) N-(3,4-dimethoxybenzyl-4-((2-(4-fluoro-3-(trifluoromethyl)phenyl)-3-oxo-6,7-dihydro-2H-pyrazolo[4,3-c]pyridin-5(3H)-yl)methyl)benzamide

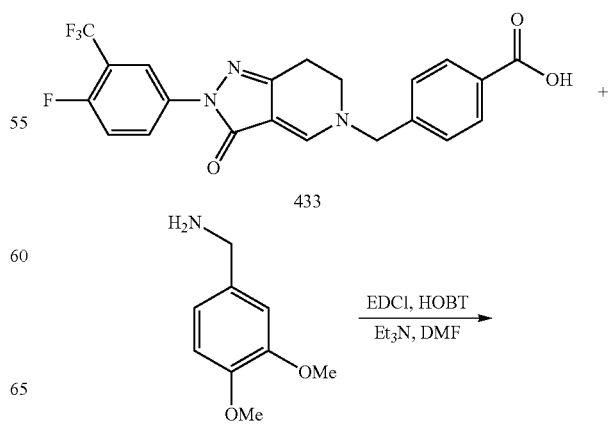

-continued

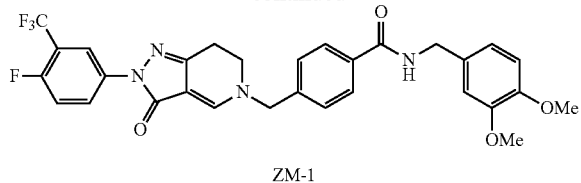
ZM-1

Compound 433 (6.1 g, 14 mmol) and 3,4-dimethoxy benzylamine (2.8 g, 16.8 mmol) were dissolved in 200 mL DMF. HOBT (100 mg) and triethylamine (5 ml, 35.6 mmol) were added successively, and the mixture was stirred at room temperature for 10 minutes. Then EDCI (6.6 g, 35.6 mmol) was added and the mixture was stirred overnight at room temperature. On next day, TLC monitored that the starting materials were entirely reacted. The reaction solution was poured into 600 mL of ice water to precipitate the solid. The solid was collected and washed with 5% citric acid solution and water successively, and dried to obtain 7.5 g of product. After further purification, 100 mL of solution of solid in methylene chloride/petroleum ether (1:5) was stirred for 30 minutes and the solid was collected. The procedure was repeated for three times to obtain 6.9 g of white solid, yield 84%, HPLC>99.74%.

ZM-1
$^1$H NMR (300 MHz, CDCl$_3$) δ 8.23-8.21 (m, 2H), 7.98 (s, 1H), 7.84 (d, J=8.1 Hz, 2H), 7.35 (d, J=8.1 Hz, 2H), 7.21-7.14 (m, 1H), 6.92-6.83 (m, 3H), 6.33 (t, 1H), 4.65 (s, 2H), 4.60 (d, J=5.7 Hz, 2H), 3.88 (s, 6H), 3.55-3.50 (t, 2H), 2.92-2.87 ppm (t, 2H)

The following compounds were obtained by using the same method:

ZM-6
$^1$H NMR (300 MHz, CDCl$_3$) δ 8.26-8.24 (m, 2H), 7.95 (s, 1H), 7.54 (d, J=8.1 Hz, 2H), 7.33 (d, J=8.1 Hz, 2H), 7.21-7.10 (m, 1H), 6.93-6.86 (m, 3H), 6.75 (t, 1H), 4.68 (s, 2H), 4.63 (d, J=5.7 Hz, 2H), 3.88 (s, 6H), 3.56-3.510 (t, 2H), 2.92-2.87 (t, 2H), 2.90 ppm (s, 3H).

ZM-7
$^1$H NMR (300 MHz, CDCl$_3$) δ 8.14-8.12 (m, 1H), 8.01-7.90 (m, 4H), 7.62 (s, 1H), 7.42-7.40 (m, 1H), 7.33-7.30 (m, 1H), 7.05-7.02 (m, 1H), 6.75-6.71 (m, 2H), 6.64-6.61 (m, 1H), 4.52 (s, 2H), 4.44 (d, J=5.7 Hz, 2H), 3.73 (s, 3H), 3.71 (s, 3H), 3.43-3.38 (t, 2H), 2.63-2.58 ppm (t, 2H)

ZM-8
$^1$H NMR (300 MHz, CDCl$_3$) δ 8.25-8.21 (m, 2H), 7.92 (s, 1H), 7.84 (d, J=8.1 Hz, 2H), 7.35 (d, J=8.1 Hz, 2H), 7.33-7.30 (m, 5H), 7.21-7.14 (m, 1H), 6.62 (t, 1H), 4.65 (s, 2H), 4.60 (d, J=5.7 Hz, 2H), 3.53-3.48 (t, 2H), 2.89-2.84 ppm (t, 2H)

ZM-9
$^1$H NMR (300 MHz, CDCl$_3$) δ 8.27-8.21 (m, 2H), 7.92 (s, 1H), 7.85 (d, J=8.1 Hz, 2H), 7.35 (d, J=8.1 Hz, 2H), 7.30-7.28 (m, 1H), 7.20-7.15 (t, 1H), 6.95-6.87 (m, 3H), 6.36 (t, 1H), 4.65 (s, 2H), 4.63 (d, J=5.7 Hz, 2H), 3.81 (s, 3H), 3.54-3.50 (t, 2H), 2.92-2.87 ppm (t, 2H)

ZM-10
$^1$H NMR (300 MHz, CDCl$_3$) δ 8.24-8.21 (m, 2H), 7.95 (s, 1H), 7.82 (d, J=8.1 Hz, 2H), 7.33 (d, J=8.1 Hz, 2H), 7.18-7.15 (m, 1H), 6.13 (s, 1H), 4.65 (s, 2H), 3.56-3.50 (m, 4H), 3.02 (s, 3H), 2.92-2.86 (t, 2H), 1.27-1.24 ppm (t, 3H)

ZM-11
$^1$H NMR (300 MHz, CDCl$_3$) δ 8.22-8.21 (m, 2H), 7.97 (s, 1H), 7.83 (d, J=8.1 Hz, 2H), 7.34 (d, J=8.1 Hz, 2H), 7.21-7.14 (m, 1H), 6.46 (s, 2H), 6.31 (t, 1H), 4.64 (s, 2H), 4.61 (d, J=5.7 Hz, 2H), 3.90 (s, 9H), 3.54-3.50 (t, 2H), 2.92-2.86 ppm (t, 2H)

ZM-12
$^1$H NMR (300 MHz, CDCl$_3$) δ 8.23-8.21 (m, 2H), 7.92 (s, 1H), 7.84 (d, J=8.1 Hz, 2H), 7.35 (d, J=8.1 Hz, 2H), 7.21-7.14 (m, 1H), 6.85-6.78 (m, 3H), 6.38 (t, 1H), 5.95 (s, 2H), 4.65 (s, 2H), 4.54 (d, J=5.7 Hz, 2H), 3.54-3.50 (t, 2H), 2.91-2.87 ppm (t, 2H)

ZM-13
$^1$H NMR (300 MHz, CDCl$_3$) δ 8.24-8.21 (m, 2H), 7.96 (s, 1H), 7.83 (d, J=8.1 Hz, 2H), 7.37 (d, J=8.1 Hz, 2H), 7.21-7.14 (m, 1H), 6.88-6.83 (m, 3H), 6.45 (t, 1H), 5.96 (s, 2H), 4.62 (s, 2H), 4.60 (d, J=5.7 Hz, 2H), 3.55-3.50 (t, 2H), 2.92-2.87 ppm (t, 2H)

ZM-14
$^1$H NMR (300 MHz, CDCl$_3$) δ 8.23-8.21 (m, 2H), 7.92 (s, 1H), 7.82 (d, J=8.1 Hz, 2H), 7.38-7.36 (m, 5H), 7.35 (d, J=8.1 Hz, 2H), 7.21-7.14 (m, 1H), 6.38 (d, 1H), 5.36-5.32 (m, 1H), 4.64 (s, 2H), 3.53-3.48 (t, 2H), 2.90-2.85 (t, 2H), 1.52 ppm (d, 3H)

ZM-15
$^1$H NMR (300 MHz, CDCl$_3$) δ 8.24-8.22 (m, 2H), 7.92 (s, 1H), 7.82 (d, J=8.1 Hz, 2H), 7.33 (d, J=8.1 Hz, 2H), 7.21-7.15 (m, 1H), 6.16 (t, 1H), 4.65 (s, 2H), 3.55-3.51 (t, 2H), 3.34-3.29 (t, 2H), 2.91-2.87 (t, 2H), 1.86-1.58 (m, 5H), 1.28-1.21 (m, 4H), 1.06-1.0.98 ppm (m, 2H)

ZM-16
$^1$H NMR (300 MHz, CDCl$_3$) δ 8.26-8.25 (m, 2H), 7.92 (s, 1H), 7.83 (d, J=8.1 Hz, 2H), 7.45-7.43 (m, 1H), 7.35 (d, J=8.1 Hz, 2H), 7.33-7.30 (m, 1H), 6.89-6.85 (m, 3H), 6.43 (t, 1H), 4.63 (s, 2H), 4.58 (d, J=5.7 Hz, 2H), 3.88 (s, 6H), 3.53-3.48 (t, 2H), 2.92-2.87 ppm (t, 2H)

ZM-17
$^1$H NMR (300 MHz, CDCl$_3$) δ 8.04-8.00 (m, 3H), 7.81-7.78 (m, 4H), 7.28 (d, J=8.1 Hz, 2H), 6.87-6.80 (m, 3H), 4.64 (s, 2H), 4.51 (t, 1H), 3.81 (s, 6H), 3.47-3.44 (t, 2H), 2.83-2.78 ppm (t, 2H)

ZM-18
$^1$H NMR (300 MHz, CDCl$_3$) δ 8.06 (s, 1H), 7.91-7.88 (d, J=8.4 Hz, 1H), 7.85-7.82 (d, J=8.1 Hz, 2H), 7.77-7.74 (d, J=8.4 Hz, 1H), 7.42-7.39 (t, 1H), 7.28 (d, J=8.1 Hz, 2H), 6.89-6.80 (m, 3H), 6.30 (t, 1H), 4.65 (s, 2H), 4.56 (d, 2H), 3.85 (s, 6H), 3.55-3.50 (t, 2H), 2.96-2.91 ppm (t, 2H)

ZM-19
$^1$H NMR (300 MHz, CDCl$_3$) δ 8.24-8.22 (m, 2H), 7.95 (s, 1H), 7.81-7.77 (m, 2H), 7.38-7.35 (m, 1H), 7.25-7.20 (m, 1H), 6.89-6.85 (m, 3H), 6.43 (t, 1H), 4.63 (s, 2H), 4.58 (d, J=5.7 Hz, 2H), 3.89 (s, 6H), 3.59-3.53 (t, 2H), 2.93-2.87 (t, 2H), 2.37 ppm (s, 3H)

ZM-20
$^1$H NMR (300 MHz, CDCl$_3$) δ 8.24-8.21 (m, 2H), 7.94 (s, 1H), 7.83 (d, J=8.1 Hz, 2H), 7.32 (d, J=8.1 Hz, 2H), 7.25-7.20 (m, 1H), 6.91 (d, J=7.2 Hz, 1H), 6.65 (d, J=11.1 Hz, 1H), 6.66 (t, 1H), 4.64 (s, 2H), 4.61 (d, J=5.7 Hz, 2H), 3.85 (s, 6H), 3.54-3.50 (t, 2H), 2.90-2.87 (t, 2H)

ZM-21
$^1$H NMR (300 MHz, CDCl$_3$) δ 8.23-8.21 (m, 2H), 7.93 (s, 1H), 7.81 (d, J=8.1 Hz, 2H), 7.36 (d, J=8.1 Hz, 2H), 7.21-7.14 (m, 1H), 7.02-6.98 (m, 2H), 6.84 (d, 1 h), 6.39 (s, 1H), 4.64 (s, 2H), 3.87 (s, 3H), 3.86 (s, 3H), 3.53-3.48 (t, 2H), 2.90-2.85 (t, 2H), 1.84 ppm (s, 6H)

ZM-22
$^1$H NMR (300 MHz, CDCl$_3$) δ 8.23-8.21 (m, 2H), 7.92 (s, 1H), 7.82 (d, J=8.1 Hz, 2H), 7.33 (d, J=8.1 Hz, 2H), 7.21-7.14 (m, 1H), 6.90-6.81 (m, 3H), 6.39 (t, 1H), 4.64 (s,

2H), 4.56 (d, J=5.7 Hz, 2H), 4.12 (t, 2H), 3.86 (s, 3H), 3.54-3.50 (t, 2H), 2.90-2.85 (t, 2H), 1.43 ppm (t, 3H)

ZM-23

$^1$H NMR (300 MHz, CDCl$_3$) δ 8.23-8.21 (m, 2H), 7.91 (s, 1H), 7.85 (d, J=8.1 Hz, 2H), 7.34 (d, J=8.1 Hz, 2H), 7.21-7.14 (m, 1H), 6.90-6.81 (m, 3H), 6.35 (t, 1H), 4.64 (s, 2H), 4.58 (d, J=5.7 Hz, 2H), 4.12 (t, 2H), 3.86 (s, 3H), 3.54-3.50 (t, 2H), 2.91-2.85 (t, 2H), 1.44 ppm (t, 3H)

ZM-27

$^1$H NMR (300 MHz, CDCl$_3$) δ 8.23-8.21 (m, 2H), 8.01 (s, 1H), 7.87 (d, J=8.1 Hz, 2H), 7.36 (d, J=8.1 Hz, 2H), 7.20-7.16 (m, 2H), 6.92-6.90 (m, 1H), 6.78-6.25 (t, 1H), 6.58 (t, 1H), 4.65 (s, 2H), 4.61 (d, J=5.4 Hz, 2H), 3.86 (s, 3H), 3.55-3.50 (t, 2H), 2.91-2.88 ppm (t, 2H)

ZM-28

$^1$H NMR (300 MHz, CDCl$_3$) δ 8.24-8.21 (m, 2H), 7.92 (s, 1H), 7.82 (d, J=8.4 Hz, 2H), 7.32 (d, J=8.4 Hz, 2H), 7.17-7.13 (m, 1H), 6.86-6.66 (m, 3H), 6.35 (t, 1H), 4.63 (s, 2H), 3.86 (s, 3H), 3.84 (s, 3H), 3.52-3.47 (t, 2H), 2.89-2.85 (t, 2H), 1.32 ppm (s, 4H)

ZM-29

$^1$H NMR (300 MHz, CDCl$_3$) δ 8.23-8.20 (m, 2H), 7.92 (s, 1H), 7.84 (d, J=8.4 Hz, 2H), 7.35 (d, J=8.4 Hz, 2H), 7.20-7.15 (m, 1H), 6.86-6.83 (m, 3H), 6.38 (t, 1H), 4.65 (s, 2H), 4.57 (d, J=6 Hz, 2H), 4.51 (m, 1H), 3.85 (s, 3H), 3.55-3.50 (t, 2H), 2.91-2.86 (t, 2H), 1.36 ppm (d, J=6.3 Hz, 6H)

ZM-30

$^1$H NMR (300 MHz, CDCl$_3$) δ 8.19-8.14 (m, 2H), 7.77 (d, J=8.4 Hz, 2H), 7.40 (d, J=8.4 Hz, 2H), 7.30-7.28 (m, 1H), 7.17-7.14 (m, 1H), 6.96-6.91 (m, 2H), 6.86-6.82 (m, 1H), 6.38 (t, 1H), 4.65 (d, J=6 Hz, 2H), 3.81 (s, 3H), 3.60 (q, 2H), 3.19 (m, 1H), 3.00 (dd, J1=10.5, J2=1.5 Hz, 1H), 2.72-2.70 (m, 1H), 2.68-2.63 (m, 1H), 2.22-2.19 (m, 1H), 2.07-2.04 (m, 1H), 1.59 ppm (s, 3H)

ZM-31

$^1$H NMR (300 MHz, CDCl$_3$) δ 8.23-8.21 (m, 2H), 7.89 (s, 1H), 7.85 (d, J=8.1 Hz, 2H), 7.35 (d, J=8.1 Hz, 2H), 7.20-7.16 (m, 2H), 6.77-6.25 (t, 1H), 6.75-6.23 (t, 1H), 6.59 (t, 1H), 4.65 (s, 2H), 4.64 (d, J=5.4 Hz, 2H), 3.55-3.50 (t, 2H), 2.92-2.88 ppm (t, 2H)

ZM-32

$^1$H NMR (300 MHz, CDCl$_3$) δ 8.23-8.21 (m, 2H), 7.90 (s, 1H), 7.85 (d, J=8.1 Hz, 2H), 7.34 (d, J=8.1 Hz, 2H), 7.18-7.13 (m, 2H), 6.95-6.93 (m, 1H), 6.82-6.30 (t, 1H), 6.55 (t, 1H), 4.65 (s, 2H), 4.58 (d, J=5.4 Hz, 2H), 3.87 (s, 3H), 3.55-3.50 (t, 2H), 2.91-2.88 ppm (t, 2H)

Preparation Example 4 N-(3,4-dimethoxybenzyl-4-((2-(4-fluoro-3-(trifluoromethyl)phenyl)-1-methyl-3-oxo-2,3,6,7-tetrahydro-1H-pyrazolo[4,3-c]pyridin-5(3H)-yl)methyl)benzamide (1) Methyl 4-((2-(2-(4-fluoro-3-(trifluoromethyl)phenyl)-1H-methyl-3oxo-2,3,6,7-tetrahydro-1H-pyrazolo[4,3-c]pyridin-5(4H)-yl)methyl)benzoic acid

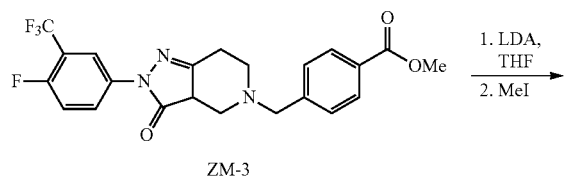

ZM-3

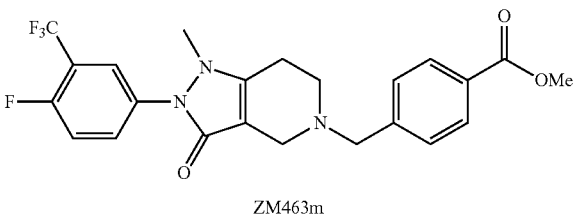

ZM463m

Under argon atmosphere, compound ZM-3 (40 mg, 0.089 mmol) was dissolved in 5 mL of anhydrous THF. The mixture was cooled to 0° C., and LDA (2M, 0.1 mL) was slowly added dropwise, MeI (40 L) was added after the mixture was stirred for 10 minutes at this temperature. The mixture was further stirred at 0° C. for 0.5 hour, warmed to room temperature and stirred for 2 hours. TLC monitored that the starting materials were entirely reacted. The reaction was quenched with saturated ammonium chloride, extracted with ethyl acetate (3 times). Water was added into the organic phase. After it was washed with saturated brine, dried over anhydrous sodium sulfate, concentrated and passed through the column (DCM/MeOH=50/1), 25 mg of product was obtained (yield 60%).

$^1$H NMR (300 MHz, CDCl$_3$) δ 8.02 (d, J=8.1 Hz, 2H), 7.60-7.58 (m, 2H), 7.45 (d, J=8.1 Hz, 2H), 7.27-7.24 (m, 1H), 3.93 (s, 3H), 3.78 (s, 2H), 3.33 (s, 2H), 2.97 (s, 3H), 2.81-2.77 (t, 2H), 2.63-2.59 ppm (t, 2H)

(2) 4-((2-(2-(4-fluoro-3-(trifluoromethyl)phenyl)-1H-methyl-3oxo-2,3,6,7-tetrahydro-1H-pyrazolo[4,3-c]pyridin-5(4H)-yl)methyl)benzoic acid

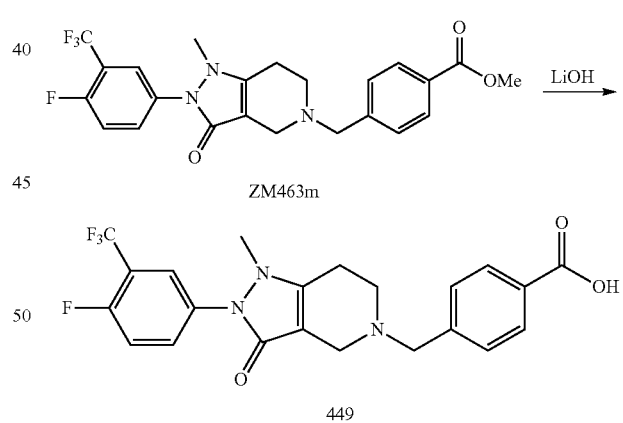

Compound ZM463m (25 mg, 0.054 mmol) was solved in 5 mL methanol. The aqueous solution of LiOH (5 mg, 0.11 mmol) 1 mL was added, and the mixture was stirred at room temperature overnight. On next day, TLC monitored that the starting materials were entirely reacted. Most of methanol was removed in vacuum under reduced pressure, and 1N HCl solution was added to adjust pH to 1-2. The mixture was extracted with ethyl acetate (3 times), and the organic phase was added with water, washed with saturate brine, dried over anhydrous sodium sulfate, and concentrated, thereby forming the compound 449 (20 mg, 90% yield).

(3) N-(3,4-dimethoxybenzyl-4-((2-(4-fluoro-3-(trifluoromethyl)phenyl)-1-methyl-3-oxo-2,3,6,7-tetrahydro-1H-pyrazolo[4,3-c]pyridin-5(3H)-yl)methyl)benzamide

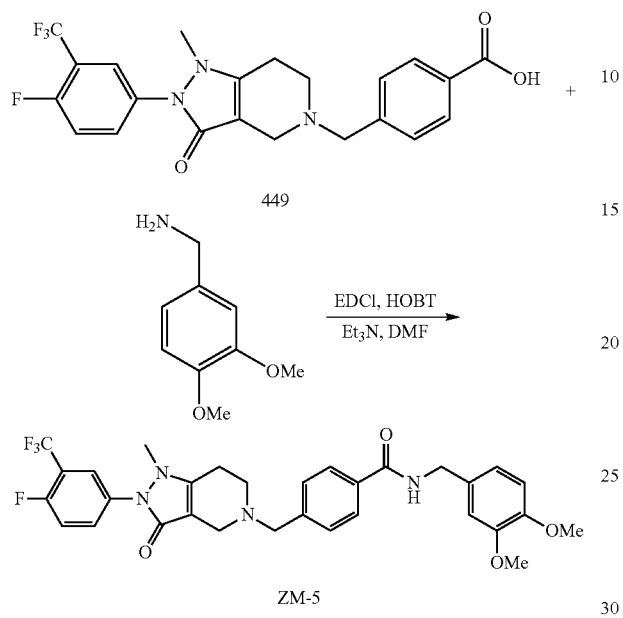

Compound 449 (20 mg, 0.045 mmol) and 3,4-dimethoxy benzylamine (15 mg, 0.089 mmol) were dissolved in 5 mL DMF. HOBT (2 mg) and triethylamine (20 ml, 0.14 mmol) were added successively. The mixture was stirred at room temperature for 10 minutes. Then EDCI (25 mg, 0.13 mmol) was added and the mixture was stirred overnight at room temperature. On next day, TLC monitored that the starting materials were entirely reacted. The reaction mixture was poured into ice water, extracted with ethyl acetate (3 times). Water was added into the organic phase. After it was washed with saturated brine, dried over anhydrous sodium sulfate, concentrated and passed through the column (DCM/MeOH=30/1), 20 mg of product was obtained (yield 76.7%).

ZM-5

$^1$H NMR (300 MHz, CDCl$_3$) δ 7.75 (d, J=8.1 Hz, 2H), 7.59-7.57 (m, 2H), 7.42 (d, J=8.1 Hz, 2H), 7.30-7.26 (m, 1H), 6.89-6.85 (m, 3H), 6.70 (t, 1H), 4.55 (d, J=5.4 Hz, 2H), 3.84 (s, 6H), 3.72 (s, 2H), 3.25 (s, 2H), 2.96 (s, 3H), 2.81-2.77 (t, 2H), 2.61-2.59 ppm (t, 2H)

The following compounds were obtained by using the same method:

ZM-24

$^1$H NMR (300 MHz, CDCl$_3$) δ 7.73 (d, J=8.1 Hz, 2H), 7.65-7.57 (m, 2H), 7.44 (d, J=8.1 Hz, 2H), 7.30-7.26 (m, 1H), 6.89-6.85 (m, 3H), 6.70 (t, 1H), 4.58 (d, J=5.4 Hz, 2H), 4.12 (t, 2H), 3.86 (s, 3H), 3.76 (s, 2H), 3.30 (s, 2H), 2.97 (s, 3H), 2.81-2.77 (t, 2H), 2.61-2.59 (t, 2H), 1.43 ppm (t, 3H)

ZM-25

$^1$H NMR (300 MHz, CDCl$_3$) δ 7.78 (d, J=8.1 Hz, 2H), 7.64-7.57 (m, 2H), 7.42 (d, J=8.1 Hz, 2H), 7.30-7.24 (m, 1H), 6.85-6.78 (m, 3H), 6.35 (t, 1H), 4.58 (d, J=5.4 Hz, 2H), 4.52 (m, 1H), 3.86 (s, 3H), 3.75 (s, 2H), 3.30 (s, 2H), 2.97 (s, 3H), 2.81-2.77 (t, 2H), 2.61-2.59 (t, 2H), 1.36 ppm (d, J=6.3 Hz, 6H)

ZM-26

$^1$H NMR (300 MHz, CDCl$_3$) δ 7.76 (d, J=8.1 Hz, 2H), 7.65-7.57 (m, 2H), 7.43 (d, J=8.1 Hz, 2H), 7.30-7.27 (m, 1H), 6.89-6.83 (m, 3H), 6.33 (t, 1H), 4.58 (d, J=5.4 Hz, 2H), 4.12 (t, 2H), 3.86 (s, 3H), 3.76 (s, 2H), 3.30 (s, 2H), 2.97 (s, 3H), 2.81-2.77 (t, 2H), 2.61-2.59 (t, 2H), 1.43 ppm (t, 3H)

Preparation Example 5 N-(3,4-dimethoxybenzyl-4-((2-(4-fluoro-3-(trifluoromethyl)phenyl)-3a-methyl-3-oxo-3a,4,6,7-tetrahydro-2H-pyrazolo[4,3-c]pyridin-5(3H)-yl)methyl)benzamide (1) Methyl 4-((2-(4-fluoro-3-(trifluoromethyl)phenyl)-3a-methyl-3-oxo-3a,4,6,7-tetrahydro-2H-pyrazolo[4,3-c]pyridin-5(3H)-yl)methyl)benzoic acid

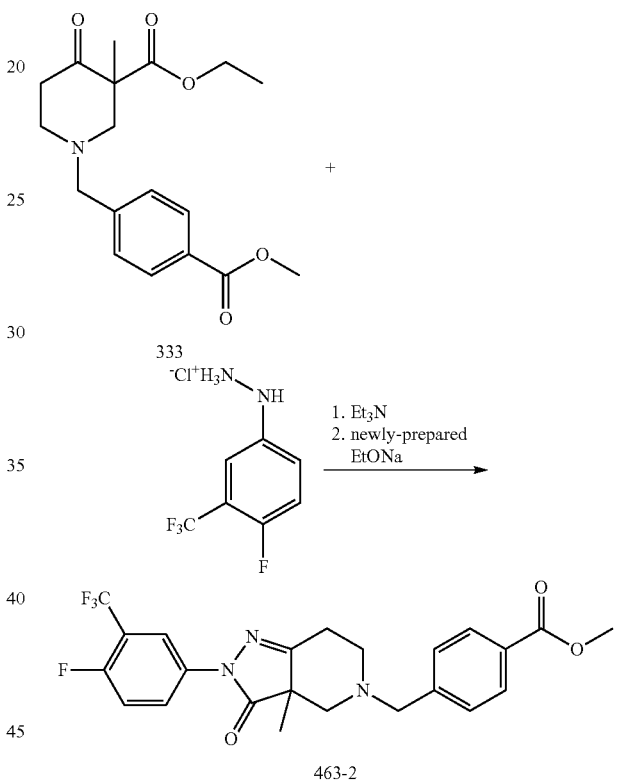

Compound 433 (340 mg, 1.02 mmol) and 3-trifluoromethyl-4-fluorophenyl hydrazine hydrochloride (276 g, 1.02 mmol) were dissolved in 10 mL of methanol, and triethylamine (0.14 mL, 1.02 mmol) was added. The mixture was heated to 60° C. and reacted for 4 h. TLC monitored the starting materials were reacted completely. The heating was stopped and the mixture was cooled to room temperature. The freshly prepared sodium methoxide (2 mmol, 60 mL) in methanol solution was added, and the mixture was stirred overnight at room temperature. On next day, the reaction mixture was poured into 20 mL 5% critic acid solution, extracted with ethyl acetate (3 times). Water was added into the organic phase. After it was washed with saturated brine, dried over anhydrous sodium sulfate, concentrated and passed through the column (petroleum ether/ethyl acetate=4/1), 160 mg of compound was obtained (yield 35%).

$^1$H NMR (300 MHz, CDCl$_3$) δ 8.19-8.15 (m, 2H), 8.02 (d, J=7.8 Hz, 2H), 7.42 (d, J=7.8 Hz, 2H), 7.20-7.18 (m, 1H), 3.93 (s, 3H), 3.74-3.58 (q, 2H), 3.24-3.19 (m, 1H), 3.00 (dd,

J 1=10.5, J2=1.5 Hz, 1H), 2.75-2.69 (m, 1H), 2.68-2.61 (m, 1H), 2.24-2.19 (m, 1H), 2.07-2.04 (m, 1H), 1.59 ppm (s, 3H).

(2) 4-((2-(4-fluoro-3-(trifluoromethyl)phenyl-3a-methyl-3-oxo-3a,4,6,7-tetrahydro-2H-pyrazolo[4,3-c]pyridin-5(3H)-yl)methyl)benzoic acid

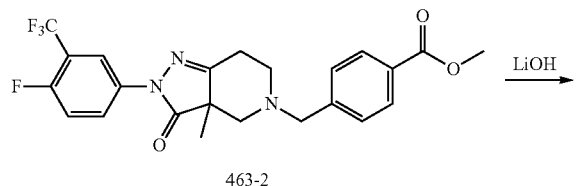

463-2

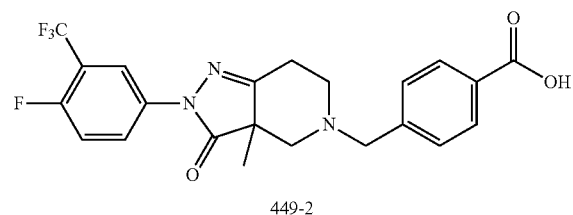

449-2

Compound 463-2 (40 mg, 0.086 mmol) was solved in 5 mL methanol. 1 mL aqueous solution of LiOH (10 mg, 0.2 mmol) was added, and the mixture was stirred at room temperature overnight. On next day, TLC monitored that the starting materials were entirely reacted. Most of methanol was removed in vacuum under reduced pressure, and 1N HCl solution was added to adjust pH to 1-2. The mixture was extracted with ethyl acetate (3 times), and water was added into the organic phase. After it was washed with saturate brine, dried over anhydrous sodium sulfate, and concentrated, product 449-2 was obtained (38 mg, 85% yield).

(3) N-(3,4-dimethoxybenzyl-4-((2-(4-fluoro-3-(trifluoromethyl)phenyl)-3a-methyl-3-oxo-3a,4,6,7-tetrahydro-2H-pyrazolo[4,3-c]pyridin-5(3H)-yl)methyl)benzamide

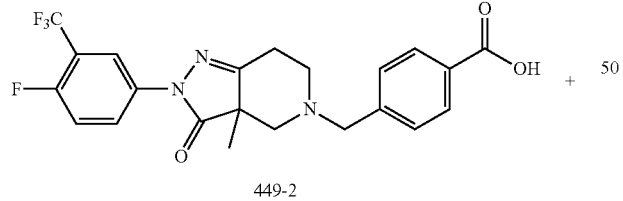

449-2

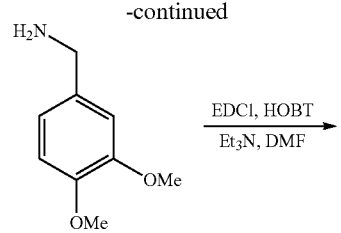

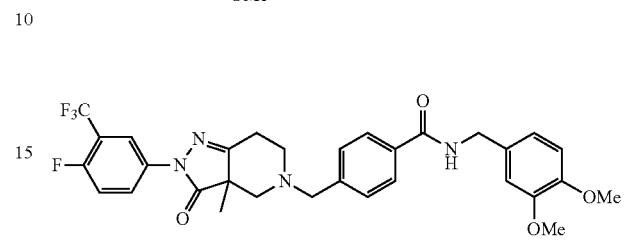

ZM-33

Compound 449-2 (20 mg, 0.045 mmol) and 3,4-dimethoxy benzylamine (15 mg, 0.089 mmol) were dissolved in 5 mL DMF. HOBT (2 mg) and triethylamine (20 ml, 0.14 mmol) were added successively. The mixture was stirred at room temperature for 10 minutes. Then EDCI (25 mg, 0.13 mmol) was added and mixture was stirred overnight at room temperature. On next day, TLC monitored that the starting materials were entirely reacted. The reaction mixture was poured into ice water, extracted with ethyl acetate (3 times). Water was added into the organic phase. After it was washed with saturated brine, dried over anhydrous sodium sulfate, concentrated and passed through the column (DCM/MeOH=30/1), the product ZM-6 was obtained (10 mg, yield 38%).

ZM-33

$^1$H NMR (300 MHz, CDCl$_3$) δ 8.19-8.14 (m, 2H), 7.78 (d, J=8.4 Hz, 2H), 7.40 (d, J=8.4 Hz, 2H), 7.17-7.14 (m, 1H), 6.92-6.83 (m, 3H), 6.38 (t, 1H), 4.63 (d, J=6 Hz, 2H), 3.81 (s, 6H), 3.68 (q, 2H), 3.18 (m, 1H), 3.00 (dd, J 1=10.5, J2=1.5 Hz, 1H), 2.72-2.70 (m, 1H), 2.68-2.63 (m, 1H), 2.22-2.19 (m, 1H), 2.07-2.04 (m, 1H), 1.59 ppm (s, 3H).

Preparation Example 6 N-(3-methoxy-4-deuterated-methoxybenzyl4-((2-(4-fluoro-3-(trifluoromethyl)phenyl)-3-oxo-6,7-dihydro-2H-pyrazolo[4,3-c]pyridin-5(3H)-yl)methyl)benzamide

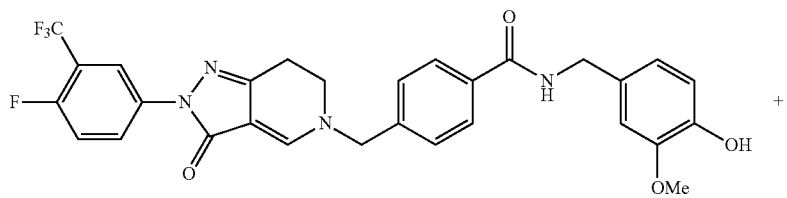

ZM-30

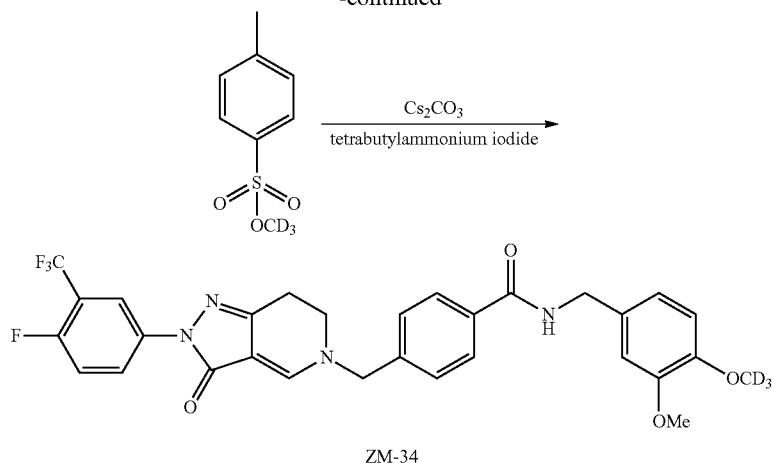

Compound ZM-30 (50 mg, 0.088 mmol) and deuteromethyl p-toluenesulfonate (50 mg, 0.25 mmol) were dissolved in 3 mL of DMF. Cesium carbonate (300 mg) and tetrabutylammonium iodide (10 mg) were added and the mixture was stirred for 2 hours under 40° C. TLC monitored that the starting materials were entirely reacted. The reaction mixture was poured into ice water, and extracted with ethyl acetate (3 times). Water was added into the organic phase. After it was washed with saturated brine, dried over anhydrous sodium sulfate, concentrated and passed through the column (DCM/MeOH=30/1), product ZM-34 was obtained (30 mg, yield 58%).

ZM-34

$^1$H NMR (300 MHz, CDCl$_3$) δ 8.23-8.21 (m, 2H), 7.95 (s, 1H), 7.83 (d, J=8.1 Hz, 2H), 7.31 (d, J=8.1 Hz, 2H), 7.18-7.14 (m, 1H), 6.90-6.83 (m, 3H), 6.56 (t, 1H), 4.64 (s, 2H), 4.56 (d, J=5.7 Hz, 2H), 3.86 (s, 3H), 3.52-3.48 (t, 2H), 2.84-2.89 ppm (t, 2H)

Experimental Example 1

1. Purpose of the experiment: To screen small molecule compounds that can activate AMPK (α2β1γ1).

2. Principle of the experiment: The peptide as substrate contains sites which can be AMPK phosphorylated. One terminal of the peptide is linked with biotin in the reaction system (containing 2 mM MgCl$_2$, 400 μM DTT, 160 nM substrate peptide, 4 μM ATP and 1.6 nM AMPK). In the biotinylated terminal, biotin can link with streptavidin-XL665 (acceptor) so as to complete the labeling. After 45 minute of phosphorylation reaction, the phosphorylated substrate (i.e., product) can bind to an antibody (labeled Donor) which recognizes the phosphorylating site, and the biotin on the other terminal can linked to streptavidin-XL665 (acceptor) so that the resulting FRET signal can be detected with PE Evision. The final AMPK activity is expressed as a ratio of the 665 nm wavelength reading to the 615 nm wavelength reading (665 nm/615 nm).

3. Detection reagent: The human AMPK (α2β1γ1) protein was obtained by expression using an *E. coli* expression system and purification. HTRF KinEASE-STK S1 kit (purchased from Cisbio's); ATP (purchased from Sigma).

4. Experimental method:

1) 200 nM AMPK (α2β1γ1) protein was incubated with 200 nM CaMKKβ at 30° C. for 4 hours in water bath to completely phosphorylate AMPK.

2) The enzyme reaction system (2 mM MgCl$_2$, 400 M DTT, 160 nM substrate peptide, 4 M ATP, and 1.6 nM AMPK) was prepared by using a white shallow plate purchased from PE. The reaction was reacted at 30° C. for 45 minutes. Phosphorylated recognizing peptides of the antibody and the XL665 Detection buffer were added and the mixture was incubated at room temperature for 3 hours before the signals were detected.

5. Experimental results: As shown in FIG. 1 and Table 1, the activation of AMPK by the small-molecule compound is shown in EC50 and activation ratio (Fold).

TABLE 1 the discovery of AMPK (α2β1γ1) small molecule allosteric activators

| Number of the compound | EC50 (μM) | Activation ratio (Fold) |
|---|---|---|
| ZM-1 | 2.1 | 3.3 |
| ZM-2 | 5.8 | 2.0 |
| ZM-3 | 9.8 | 2.8 |
| ZM-4 | 8.4 | 3.2 |
| ZM-5 | 3.3 | 3.6 |
| ZM-6 | 1.1 | 3.0 |
| ZM-7 | 4.6 | 2.7 |
| ZM-8 | 8.6 | 3.0 |
| ZM-9 | 5.3 | 2.8 |
| ZM-10 | 10.0 | 2.7 |
| ZM-11 | 7.5 | 3.5 |
| ZM-12 | 5.0 | 3.0 |
| ZM-13 | 3.3 | 2.5 |
| ZM-14 | 9.7 | 2.5 |
| ZM-15 | 5.8 | 2.2 |
| ZM-16 | 5.6 | 3.2 |
| ZM-17 | 9.5 | 2.1 |
| ZM-18 | 6.3 | 2.8 |
| ZM-19 | 5.6 | 2.6 |
| ZM-20 | 4.4 | 2.8 |
| ZM-21 | 4.0 | 2.2 |
| ZM-22 | 6.7 | 2.9 |
| ZM-23 | 5.4 | 3.0 |
| ZM-24 | 2.5 | 2.8 |
| ZM-25 | 2.5 | 3.1 |
| ZM-26 | 3.0 | 2.3 |
| ZM-27 | 5.0 | 2.3 |
| ZM-28 | 3.2 | 2.6 |
| ZM-29 | 9.7 | 2.9 |
| ZM-30 | 8.6 | 2.7 |
| ZM-31 | 5.4 | 3.1 |
| ZM-32 | 4.1 | 2.4 |
| ZM-33 | 7.8 | 2.7 |
| ZM-34 | 6.3 | 2.1 |

TABLE 1-continued the discovery of AMPK (α2β1γ1) small molecule allosteric activators

| Number of the compound | EC50 (μM) | Activation ratio (Fold) |
|---|---|---|
| A769662 | 0.02 | 3.2 |
| AMP | 0.3 | 2.6 |

6. Results and discussion

It was shown in Table 1 and FIG. 1 that this class of compounds as compound ZM-1 could significantly and allosterically activate AMPK in molecular level.

Experimental Example 2

1. Purpose of the detection: To determine whether the small molecule compounds which significantly activate AMPK at the molecular level can activate AMPK intracellularly.

2. Experimental principle: Small molecule compounds allosterically activate AMPK and cause the phosphorylation of substrate acetyl-CoA carboxylase (ACC) at Ser-79-site.

3. Detection reagents: AMPK, phospho-AMPK (T172), phospho-ACC (S79), and total ACC antibodies were purchased from Cell Signaling Technology.

4. Experimental method:

1) The cells were exchanged into serum-free medium and starved for two hours, and compounds were added to treat (in 0.4% DMSO) for 1 hour. The cells to be harvested were washed with PBS once. 1×SDS gel loading buffer (50 mM Tris (pH6.8), 100 mM DTT, 2% SDS, 10% glycerol, 0.1% bromophenol blue) was added to lysis cells (24 well plates, 70 ml per well).

2) The sample was heated at 100° C. for 10 minutes and then centrifuged at 12000 g for 10 minutes. The supernatant was subjected to SDS-PAGE electrophoresis under following condition: spacer gel: 70 volts, and separation gel: 90 volts.

3) After electrophoresis, the proteins were transferred onto nitrocellulose membrane using Biorad wet electrical transduction system. After the desired band was cut, the strips were blocked in a blocking solution (TBST, containing 5% BSA) for 1 hour at room temperature. The strips were place in a solution containing the primary antibody and incubated overnight at 4° C.

4) On next day, the target band was placed in TBST and washed at room temperature for 10 minutes (3 times). The strips were then incubated in a solution of secondary antibody (goat anti-rabbit and goat anti-mouse 1:8000 in TBST) for 1 hour at room temperature. Then TBST membrane was washed for 15 minutes (3 times), and then exposed to ECL reagents.

Figure 2:
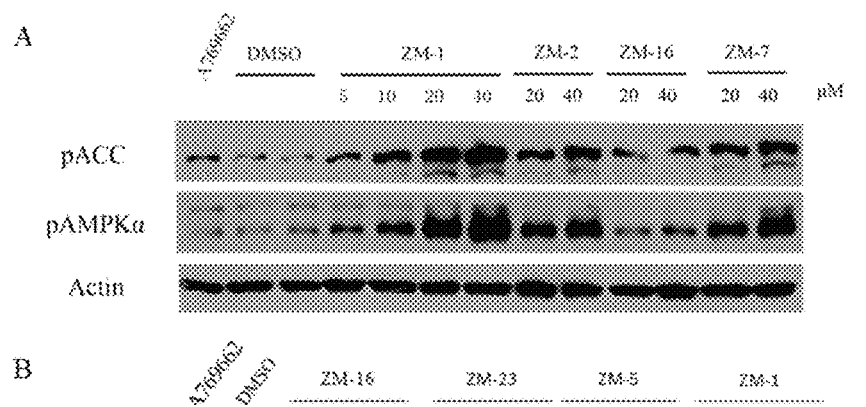
FIGS. 2A and B show stimulation of AMPK and ACC phosphorylation on L6 myotubes wherein compounds that significantly activate AMPK are selected to detect their effects on glucose uptake and AMPK dependence.
Figure 2:
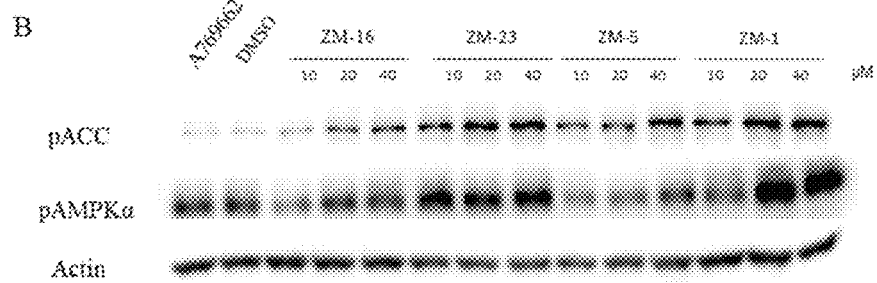

5. Experimental results:

As shown in FIGS. 2A and 2B, ZM-1 was the best activator of AMPK at the cellular level in those selected small molecules that significantly activated AMPK at the molecular level. AMPK was dose-dependently activated after treating L6 muscle cells for 1 hour, and the downstream phosphorylation levels of ACC were increased accordingly.

Figure 3:
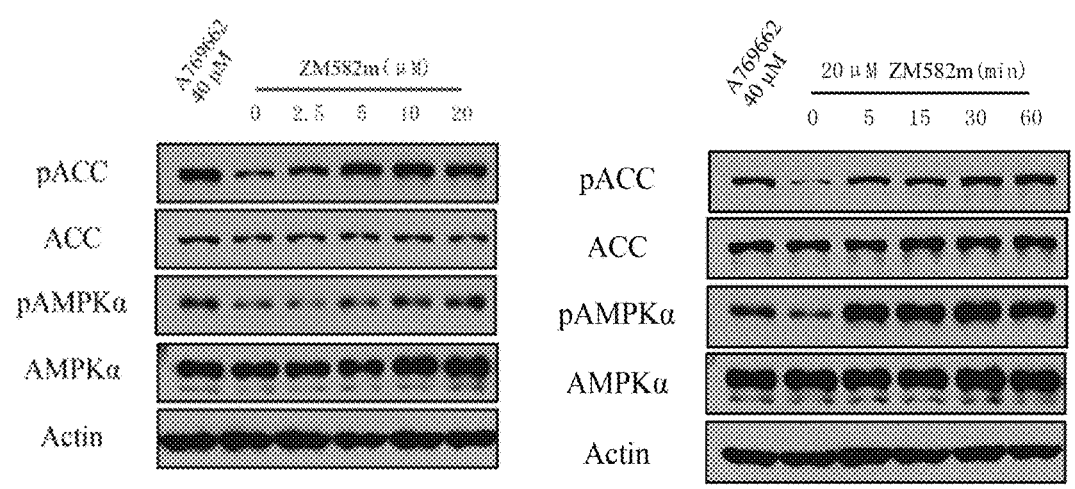
FIG. 3 shows phosphorylation of AMPK and AC at different concentrations and treatment times of ZM-1 on HepG2 cells.

As shown in FIG. 3, when HepG2 cells were treated with different concentrations of ZM-1, it could activate AMPK and upregulate phosphorylation of ACC in a concentration or gradient dependent manner.

Figure 4:
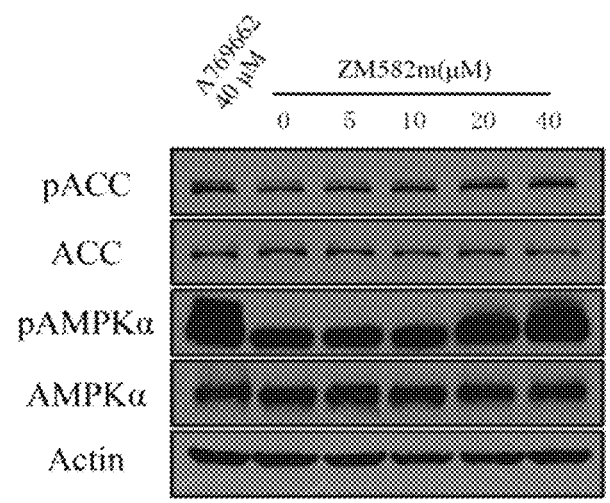
FIG. 4 shows stimulation of AMPK and ACC phosphorylation by ZM-1 on SD rat primary hepatocytes.

As shown in FIG. 4, when the primary hepatocytes of SD rats treated with different concentrations of ZM-1, it could activate AMPK and upregulate phosphorylation of ACC in a concentration or gradient dependent manner.

All documents referred to in the present invention are incorporated by reference as if each reference is cited alone as a reference in the present application. In addition, it should be understood that after reading the teachings of the present invention described above, a skilled person in the art can make various changes or modifications of the invention, and these equivalent forms also fall into the scope as defined by the appended claims of the present application.

The invention claimed is:

1. A compound of formula I, or a pharmaceutically acceptable salt thereof:

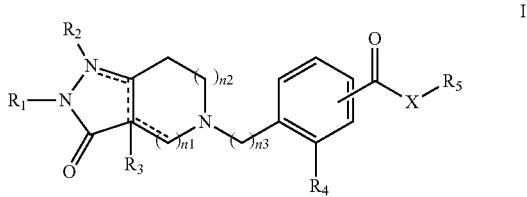

wherein the structure is:

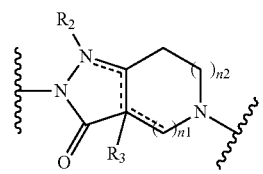

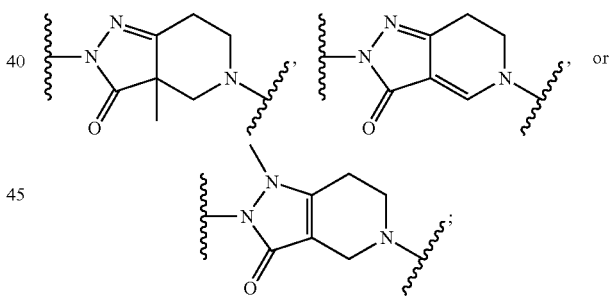

$R_1$ is selected from the group consisting of 6- to 12-membered aryl group and 5-10 membered heteroaryl in which hydrogen atoms on the group are optionally substituted with one or more substituents selected from the group consisting of halogen, C1-C4 alkyl, C1-C4 halogen substituted alkyl, adamantyl, hydroxyl, amino, nitro, substituted or unsubstituted acetoxy group (AcO), carboxyl, C1-C4 alkoxy, C1-C4 haloalkoxy, cyano, substituted or unsubstituted phenyl, and —SO$_2$—NH$_2$; wherein the term "substituted" as used with respect to the C1-C4 halogen substituted alkyl, substituted or unsubstituted acetoxygroup (AcO), and substituted or unsubstituted phenyl refers to one or more hydrogen atoms on the group being substituted with substituents selected from the group consisting of halogen, trifluoromethyl, hydroxy, amino, C1-C4 alkyl, C1-C4 alkoxy, adamantyl, and cyano;

R₄ is selected from the group consisting of H, C1-C4 alkyl, C1-C4 haloalkyl, halogen, hydroxy, amino, nitro, AcO, carboxyl, C1-C4 alkoxy, and cyano;

R₅ is selected from the group consisting of H, C1-C4 alkyl, C3-C7 cycloalkyl, C1-C4 alkylene-C3-C7 cycloalkyl, phenyl, C1-C4 alkylene phenyl, wherein hydrogen atoms on phenyl or C1-C4 alkylene phenyl are optionally substituted by one or more substituents selected from the group consisting of hydroxy, halogen, C1-C4 alkyl, C1-C4 haloalkyl, C3-C7 cycloalkyl, C1-C4 alkoxy, and C1-C4 haloalkoxy; wherein when R₅ is a phenyl-containing group, the hydrogen atoms of two adjacent carbons on the phenyl are optionally substituted by "—O—(CH₂)$_n$O—", wherein n=1, 2 or 3;

n3 is 0, 1, or 2;

X is selected from the group consisting of 0 and NR₈, wherein R₈ is selected from the group consisting of H, C1-C4 alkyl, C1-C4 haloalkyl, C3-C7 cycloalkyl, phenyl, and C1-C4 alkylene phenyl.

2. The compound of claim 1, wherein:

R₁ is selected from the group consisting of 6- to 12-membered aryl group and 5-10 membered heteroaryl group in which the hydrogen atoms on the group are optionally substituted with one or more substituents selected from the group consisting of halogen, trifluoromethyl, C1-C4 alkyl, adamantyl, hydroxyl, amino, nitro, substituted or unsubstituted acetoxygroup (AcO), carboxyl, C1-C4 alkoxy, cyano, substituted or unsubstituted phenyl, and —SO₂—NH₂;

R₄ is H or methyl;

R₅ is selected from the group consisting of C1-C4 alkyl, C3-C7 cycloalkyl, C1-C4 alkylene-C3-C7 cycloalkyl and benzyl, wherein the hydrogen atoms on benzyl are optionally substituted by one or more substituents selected from the group consisting of hydroxy, halogen, C1-C4 alkyl, C1-C4 haloalkyl, C1-C4 alkoxy, C1-C4 haloalkoxy, and C2-C4 alkylene; wherein the hydrogen atoms of two adjacent carbons on phenyl are optionally substituted by "—O—(CH₂)$_n$O—", wherein n=1, 2 or 3;

n3 is 1; and

X is O or NR₈, wherein R₈ is H or methyl.

3. The compound of claim 1, wherein:

R₁ is aryl or heteroaryl selected from the group consisting of phenyl and benzothiazolyl; in which the hydrogen atoms on the aryl or heteroaryl are optionally substituted with one or more substituents selected from the group consisting of halogen, trifluoromethyl, C1-C4 alkyl, hydroxyl, amino, nitro, substituted or unsubstituted acetoxy group (AcO), carboxyl, C1-C4 alkoxy, cyano, substituted or unsubstituted phenyl, and —SO₂—NH₂; and X is NR₈, wherein R₈ is H or methyl.

4. The compound of claim 1, wherein R₅ is selected from the group consisting of benzyl, wherein the hydrogen atoms on benzyl are optionally substituted by one or more substituents selected from the group consisting of hydroxy, halogen, C1-C4 alkyl, C1-C4 fluoroalkyl, C1-C4 fluoroalkoxy, and C2-C4 alkylene; wherein the hydrogen atoms of two adjacent carbons on phenyl structure of benzyl are optionally substituted by "—O—(CH₂)$_n$O—", wherein n=1, 2 or 3.

5. A compound selected from the group consisting of:

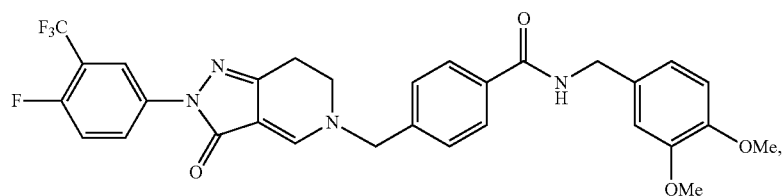

ZM-1

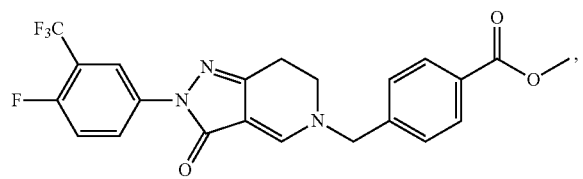

ZM-2

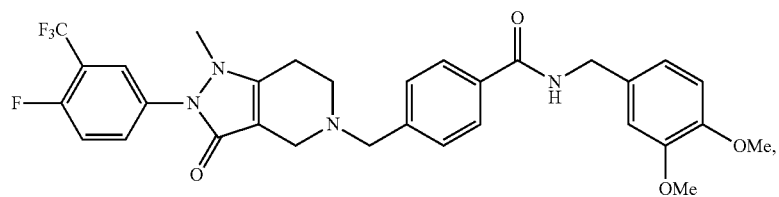

ZM-5

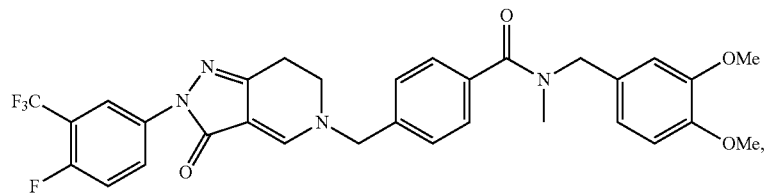

ZM-6

-continued
ZM-7
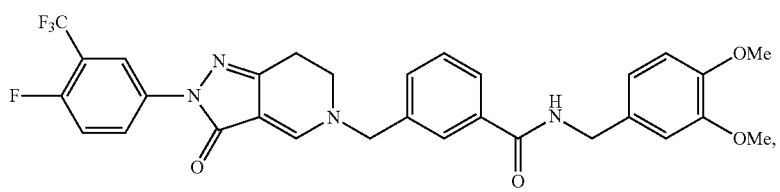
ZM-8
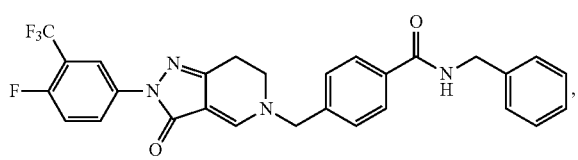
ZM-9
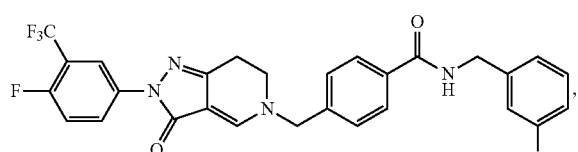
ZM-10
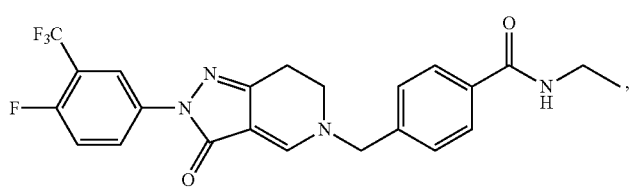
ZM-11
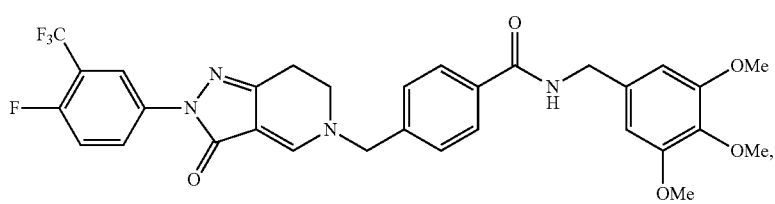
ZM-12
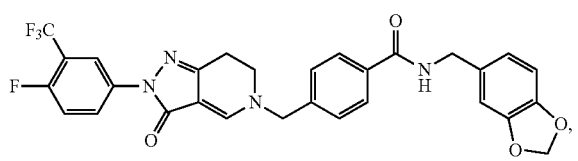
ZM-13
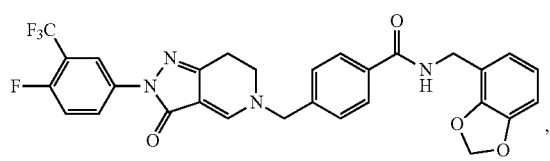
ZM-14
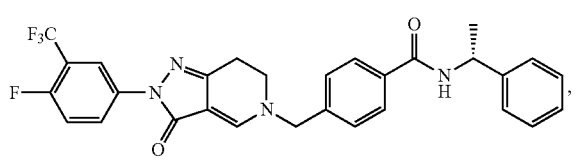
ZM-15
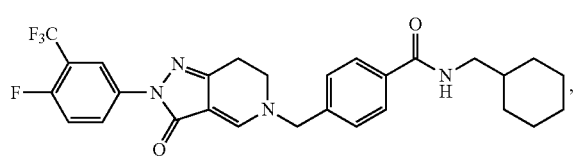
ZM-16
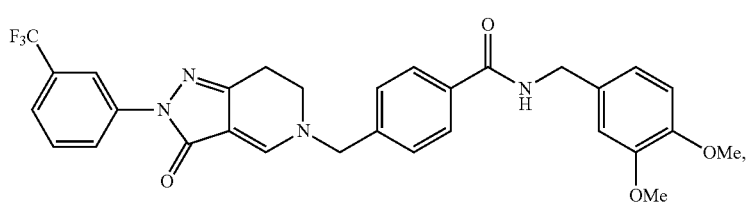
ZM-17
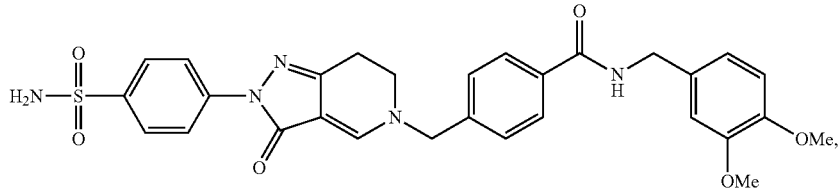

ZM-18
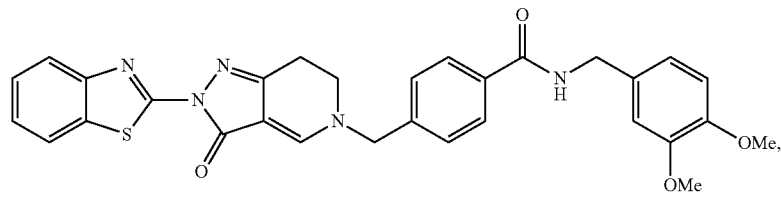
ZM-19
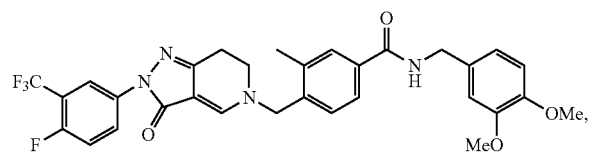
ZM-20
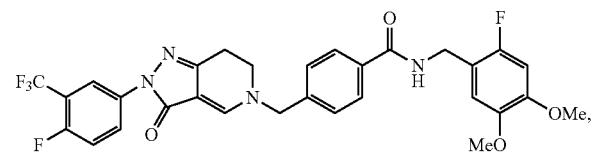
ZM-21
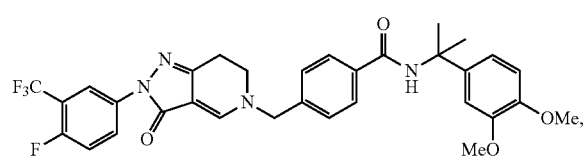
ZM-22
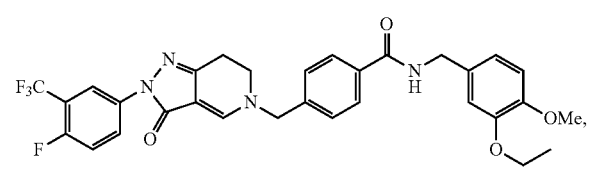
ZM-23
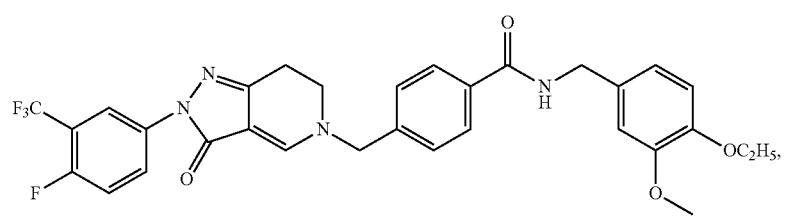
ZM-24
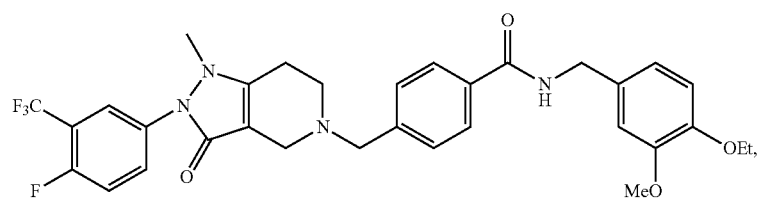
ZM-25
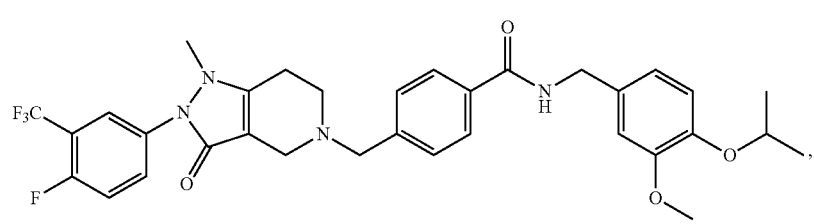
ZM-26
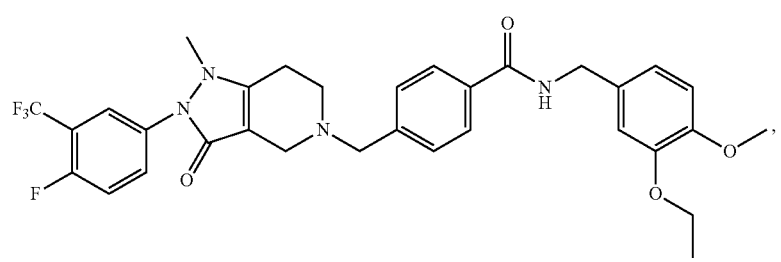

-continued
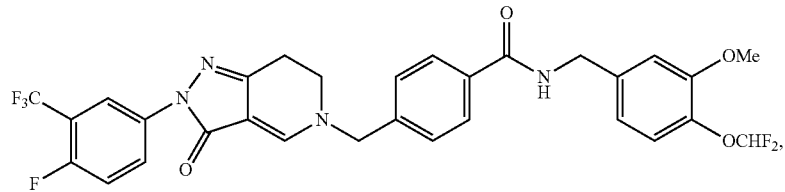
ZM-27
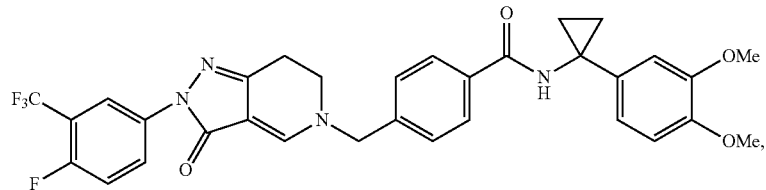
ZM-28
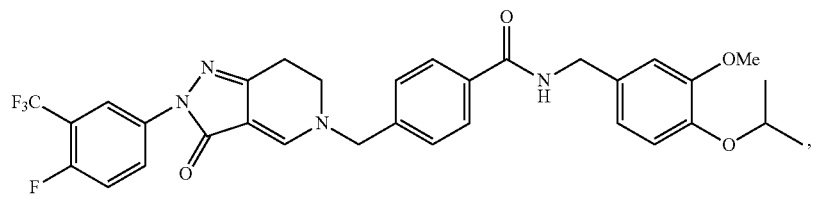
ZM-29
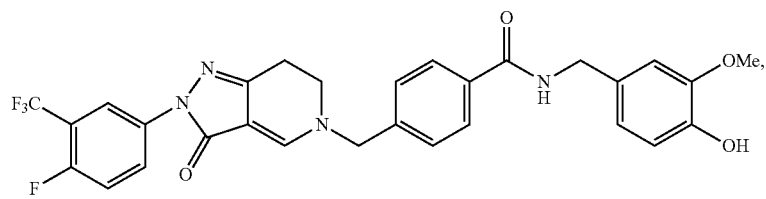
ZM-30
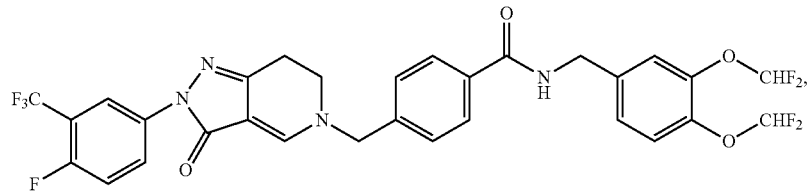
ZM-31
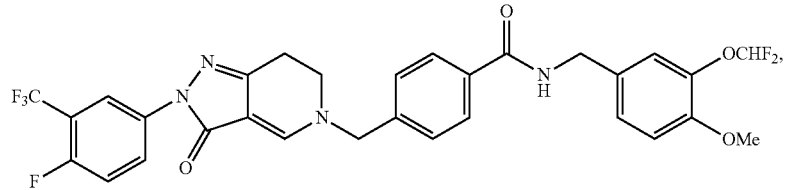
ZM-32
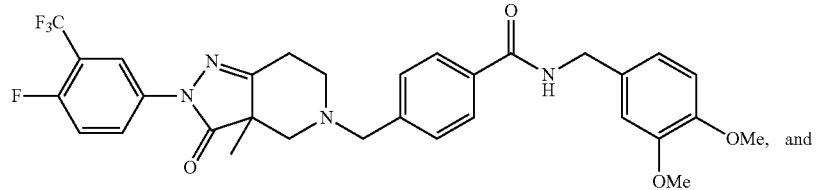
ZM-33
and -continued

ZM-34

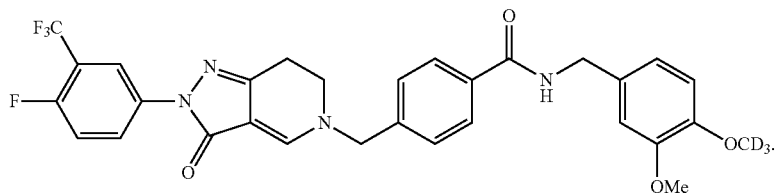

or a pharmaceutically acceptable salt thereof.

6. A preparation method of a compound of formula I of claim 1, wherein the method comprises:

(1) reacting a compound of formula Ia with a compound of formula Ib in an inert solvent, thereby forming a compound of formula I';

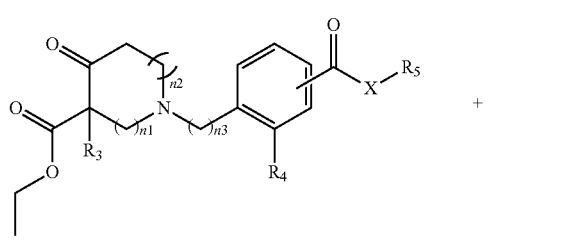

Ia

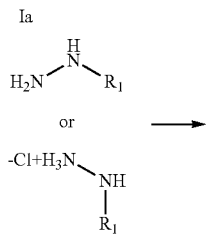

Ib

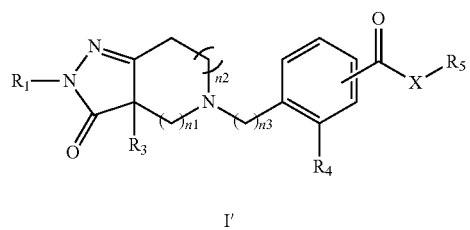

I'

(b1) optionally dehydrogenating the compound of formula I' in an inert solvent, thereby forming a compound of formula I'';

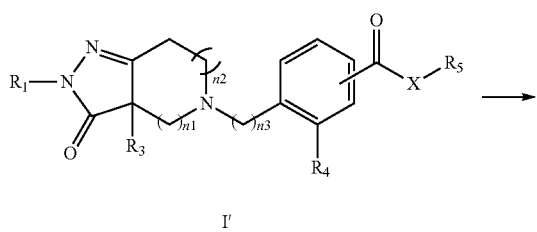

I'

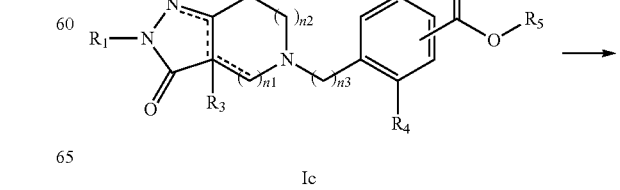

I''

(b2) optionally conducting an elimination reaction with the compound of formula I' and $R_2I$ in an inert solvent, thereby forming a compound of formula I''';

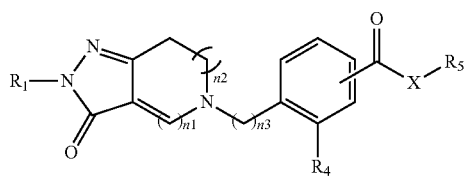

I'

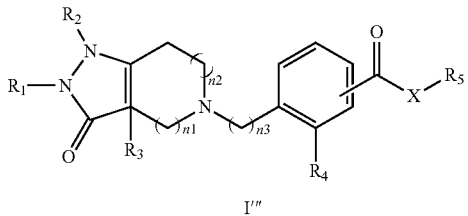

I''' wherein $R_1$, $R_4$, $R_5$, X and n3 are defined as in claim 1; each of n1 and n2 is 1; and each of $R_2$ and $R_3$ is H or methyl.

7. The preparation method of claim 6, wherein when X in formula I', I'' or I''' is O, the method further comprises:

(i) when $R_5$ is other than H, conducting a hydrolysis reaction of a formula Ic compound in an inert solvent, thereby forming a compound of formula Id;

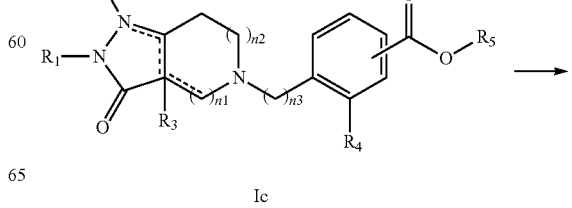

Ic

57

-continued

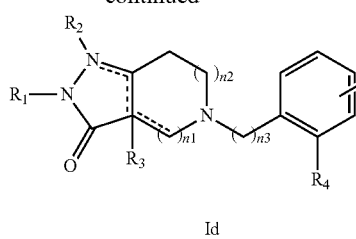

Id (ii) reacting the compound of formula Id with R₅—NH₂ in an inert solvent, thereby forming a compound of formula Ie;

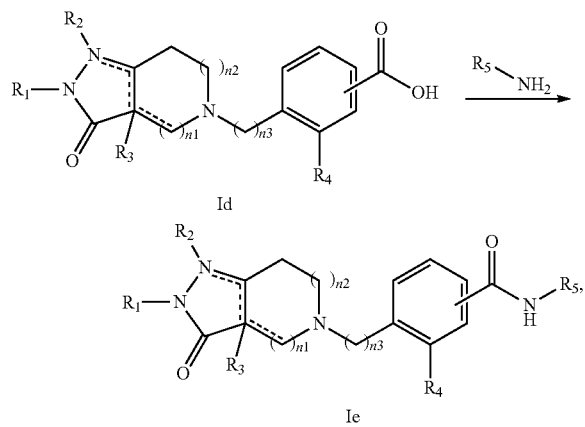

wherein the structure

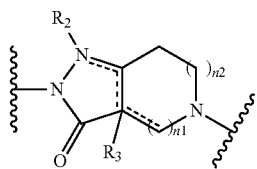

in the formula Ic, Id, and Ie is:

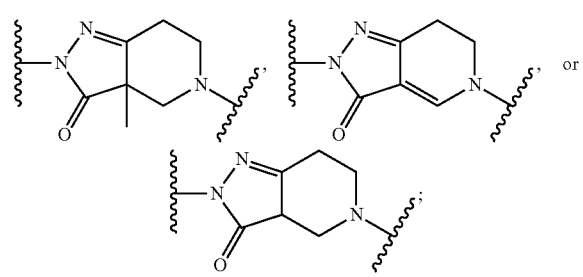

and
 wherein each group is defined as in claim 6.

8. A pharmaceutical composition comprising a therapeutically effective amount of the compound of formula I of claim 1, or a pharmaceutically acceptable salt thereof; and a pharmaceutically acceptable carrier.

9. A method of activating AMPK activity in vitro, the method comprising contacting AMPK with a compound of formula I of claim 1, or a pharmaceutically acceptable salt thereof.

10. A method of promoting phosphorylation of at least one of AMPK and ACC in vitro, the method comprising contacting AMPK and/or ACC with a compound of formula I of claim 1, or a pharmaceutically acceptable salt thereof.

11. A method of treating diabetes or obesity in a subject in need thereof, the method comprising administering to the subject the pharmaceutical composition of claim 8.

12. A pharmaceutical composition comprising a therapeutically effective amount of the compound of claim 5, or a pharmaceutically acceptable salt thereof; and a pharmaceutically acceptable carrier.

13. A method A method of activating AMPK activity in vitro, the method comprising contacting AMPK with a compound of claim 5, or a pharmaceutically acceptable salt thereof.

14. A method of promoting phosphorylation of at least one of AMPK and ACC in vitro, the method comprising contacting AMPK and/or ACC with a compound of claim 5, or a pharmaceutically acceptable salt thereof.

15. A method of treating diabetes or obesity in a subject in need thereof, the method comprising administering to the subject the pharmaceutical composition of claim 12.

* * * * *